United States Patent [19]
Cosgrove et al.

[11] Patent Number: 5,800,531
[45] Date of Patent: Sep. 1, 1998

[54] BIOPROSTHETIC HEART VALVE IMPLANTATION DEVICE

[75] Inventors: Delos M. Cosgrove, Hunting Valley, Ohio; Richard Rhee, Diamond Bar; Diana Nguyen, Santa Ana, both of Calif.

[73] Assignee: Baxter International Inc., Deerfield, Ill.

[21] Appl. No.: 723,420

[22] Filed: Sep. 30, 1996

[51] Int. Cl.$^6$ .................................................. A61F 2/24
[52] U.S. Cl. .................................................. 623/2; 623/900
[58] Field of Search .................................. 606/139, 148; 623/2, 900

[56] References Cited

U.S. PATENT DOCUMENTS

| | | |
|---|---|---|
| 4,182,446 | 1/1980 | Penny . |
| 4,501,030 | 2/1985 | Lane . |
| 4,702,250 | 10/1987 | Ovil et al. ............... 606/148 |
| 4,865,600 | 9/1989 | Carpentier et al. ........ 623/900 |
| 4,932,965 | 6/1990 | Phillips . |
| 5,032,128 | 7/1991 | Alonso . |
| 5,089,015 | 2/1992 | Ross . |
| 5,197,979 | 3/1993 | Quintero . |
| 5,290,300 | 3/1994 | Cosgrove . |
| 5,415,667 | 5/1995 | Frater . |
| 5,476,510 | 12/1995 | Eberhardt et al. . |
| 5,480,425 | 1/1996 | Ogilive . |
| 5,578,076 | 11/1996 | Krueger et al. ........... 623/900 |

FOREIGN PATENT DOCUMENTS

| | | |
|---|---|---|
| 242172A2 | 3/1987 | European Pat. Off. . |
| WO 95 14443 | 6/1995 | WIPO . |
| WO 95/17139 | 6/1995 | WIPO . |

*Primary Examiner*—Michael Powell Buiz
*Assistant Examiner*—Kevin Truong
*Attorney, Agent, or Firm*—Robert D. Buyan; Guy L. Cumberbatch

[57] ABSTRACT

In general, the present invention comprises an holding apparatus for facilitating implantation of a prosthetic heart valve within a mammalian heart. The holding apparatus generally comprises a cage or enclosure having a heart valve prosthesis retention space defined therewith. The proximal end of the holding apparatus is releasably attached to the proximal end of the heart valve prosthesis such that, when the holding apparatus is advanced in a forward direction, a "pulling" force will be exerted upon the proximal end of the prosthesis, rather than a "pushing" force being exerted upon the distal end of the prosthesis. The releasable attachment of the prosthesis to the holding apparatus may be accomplished by any suitable attachment member, and preferably comprises a number of suture threads which are passed through the prosthesis and threaded upon the holding apparatus at location(s) which are easily accessible such that the surgeon may cut the suture threads to effect release of the heart valve prosthesis, during the prosthesis implantation procedure. Also described and claimed are associated methods for utilizing the above-described holding apparatus to effect implantation of a prosthetic heart valve.

82 Claims, 9 Drawing Sheets

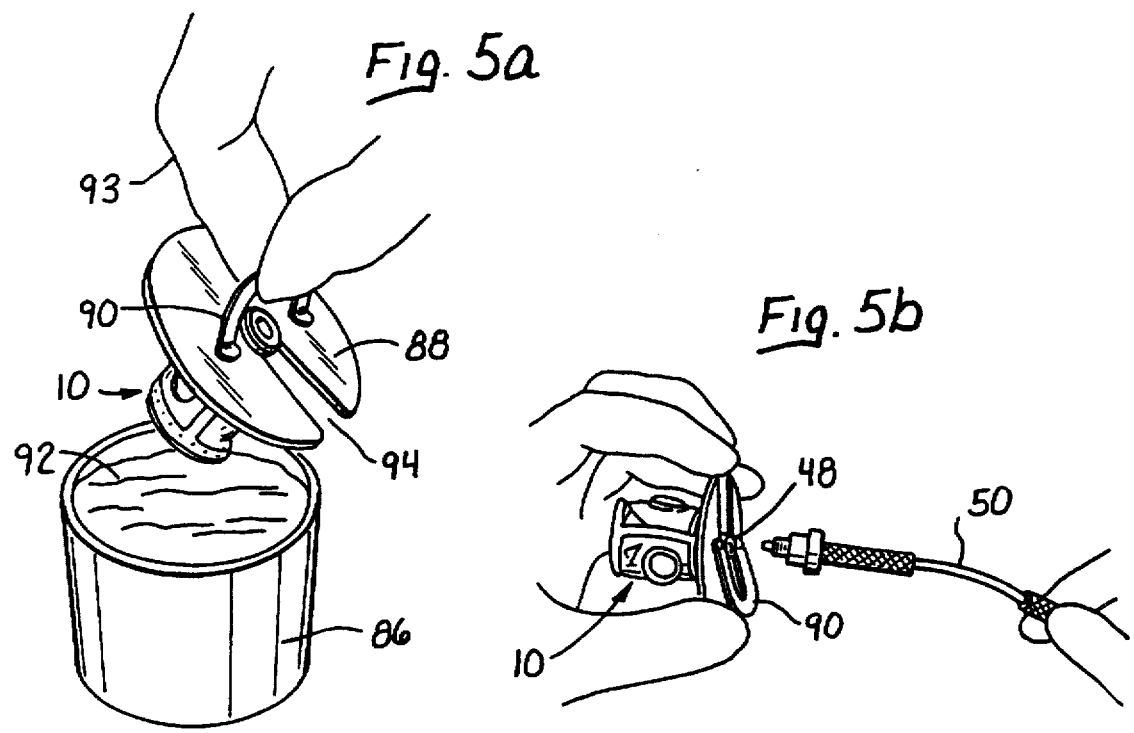
Fig. 5a
Fig. 5b
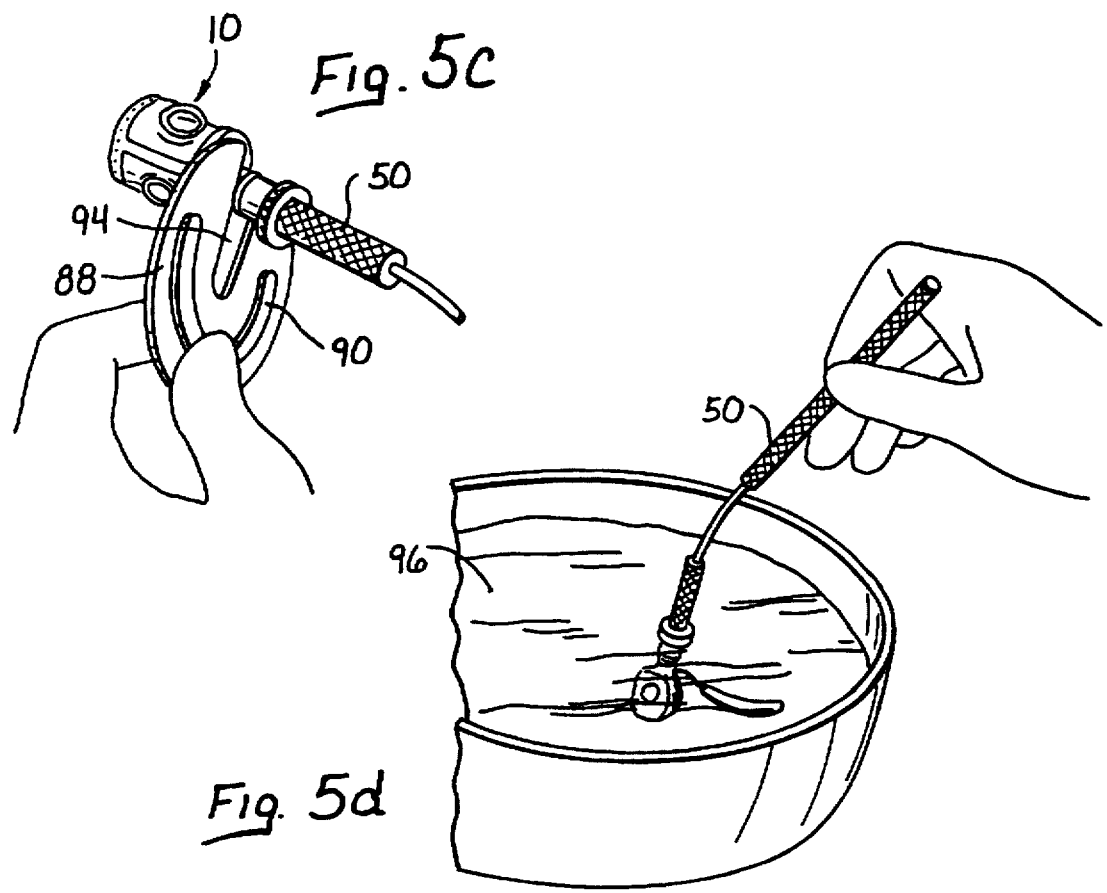
Fig. 5c
Fig. 5d

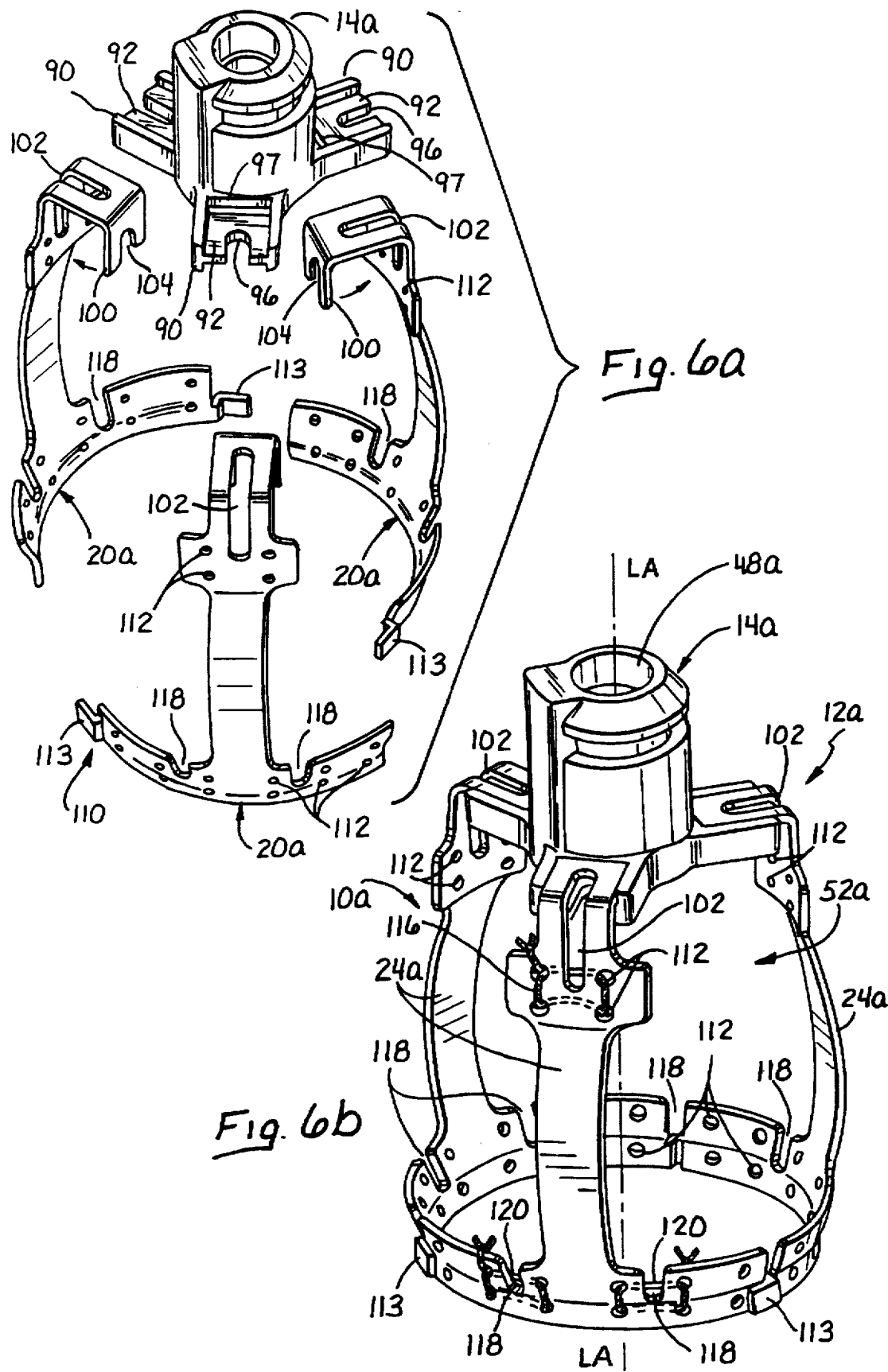

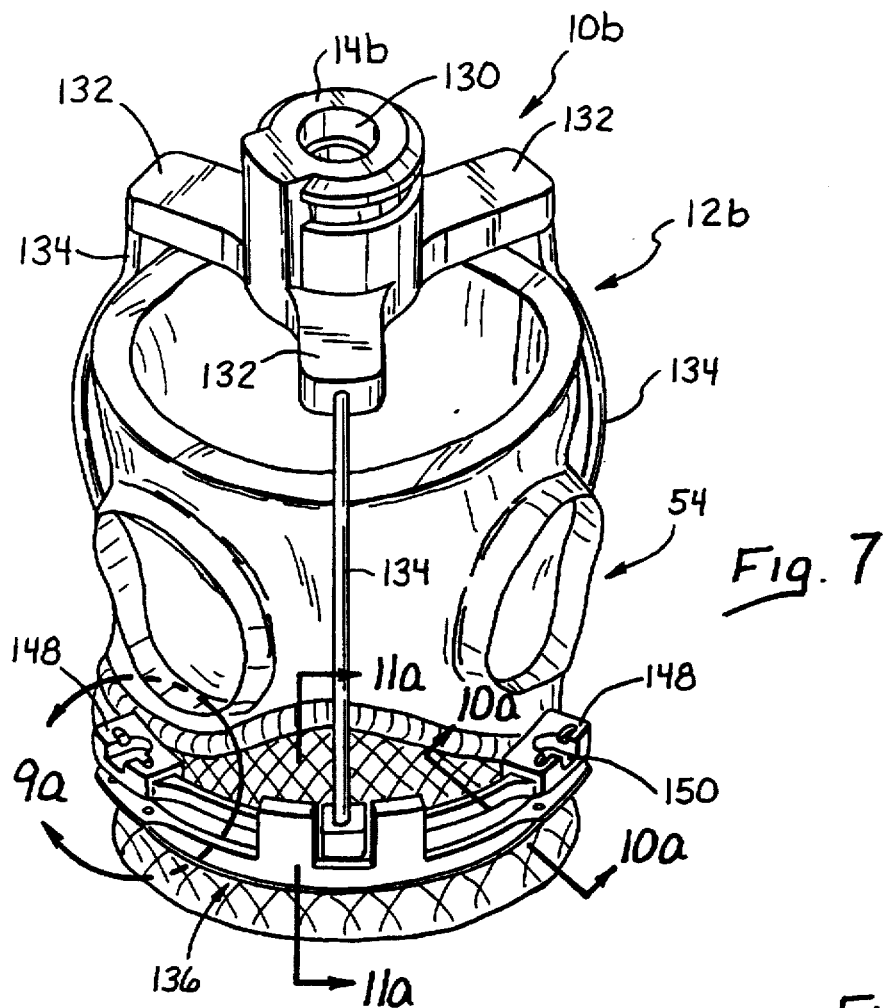
Fig. 7
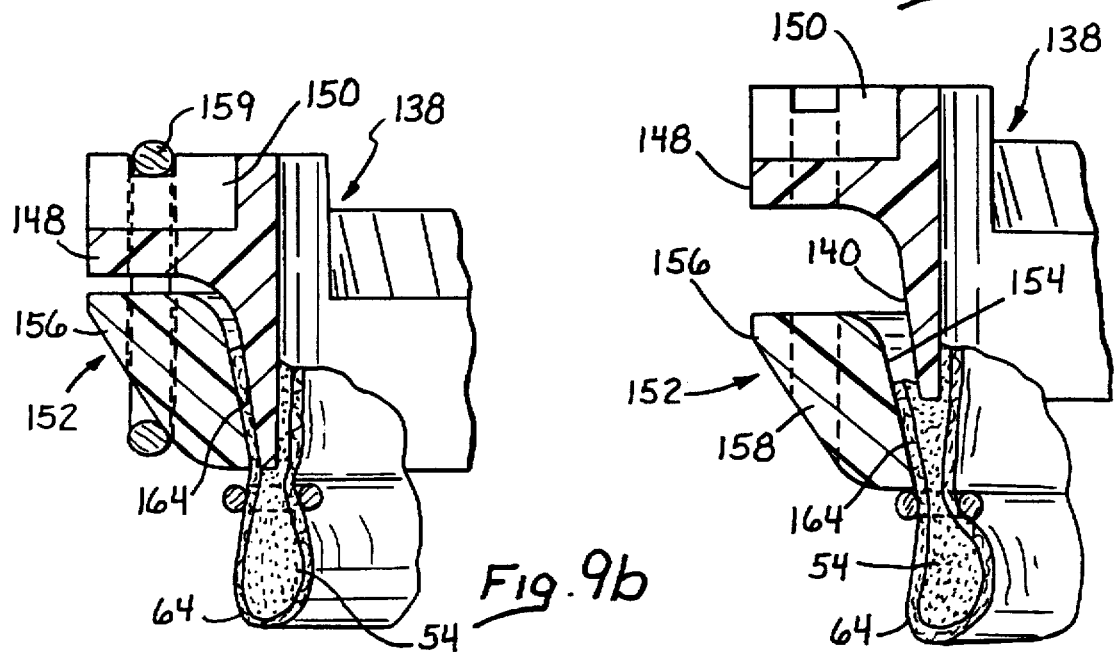
Fig. 9b
Fig. 9c

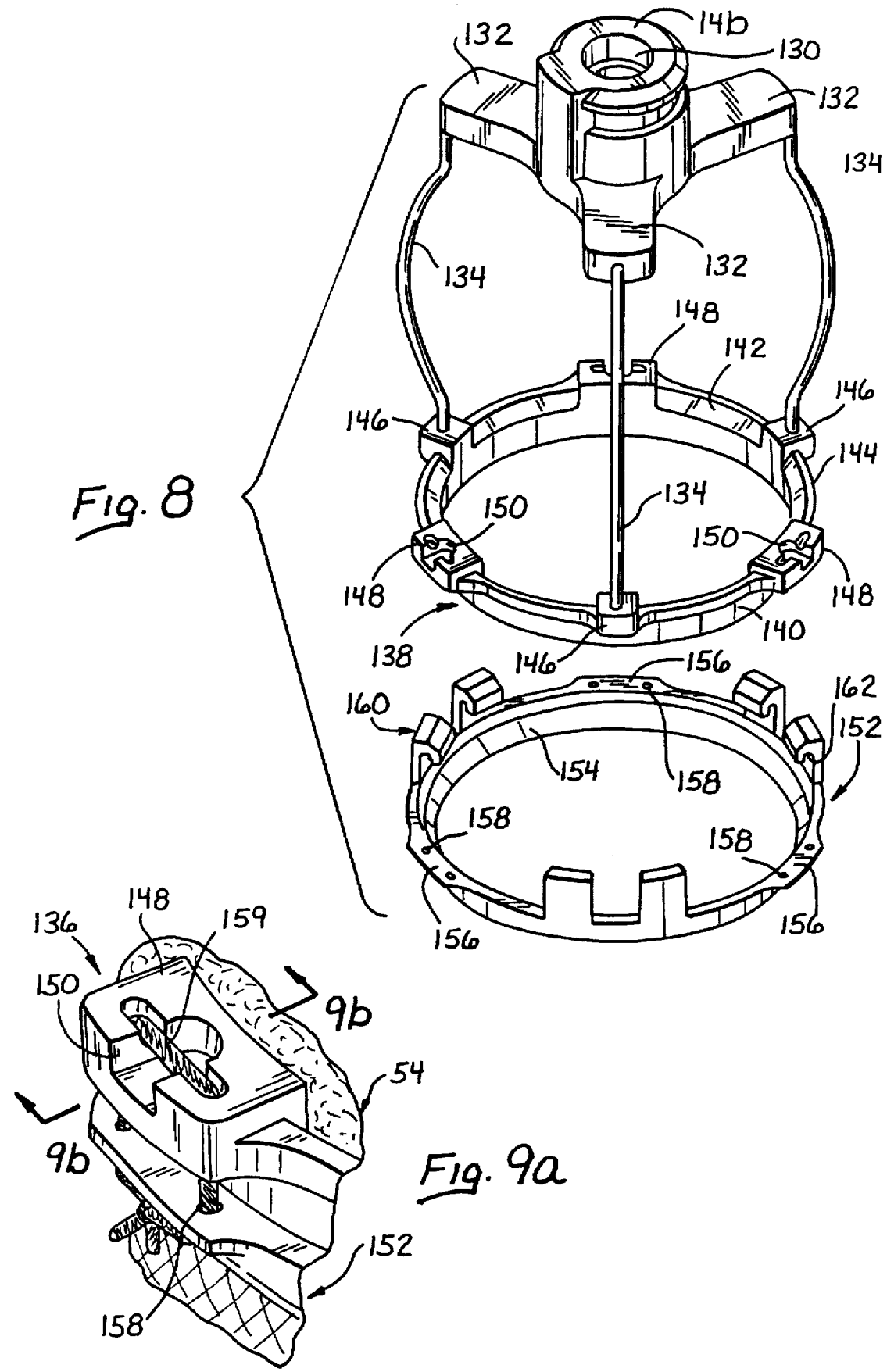

BIOPROSTHETIC HEART VALVE IMPLANTATION DEVICE

FIELD OF THE INVENTION

The present invention relates generally to medical devices, and more particularly to an apparatus for facilitating the implantation of a stentless bioprosthetic, (e.g., xeno raft, homograft, allograft) heart valve, and associated methodology.

BACKGROUND OF THE INVENTION

Among the various types of prosthetic heart valves which have heretofore been known are certain "stentless" bioprosthetic valves. One example of a stentless bioprosthetic heart valve is described in U.S. Pat. No. 5,197,979 (Quintero, et. al.), the entire disclosure of which is hereby expressly incorporated by reference.

One such stentless bioprosthetic valve is commercially available as the Edwards® PRIMA™ stentless aortic bioprosthesis (Baxter Edwards AG, Spierstrasse 5, GH6048 Horn, Switzerland). This stentless aortic bioprosthesis generally comprises a chemically-tanned porcine aortic heart valve having an adjacent segment of aorta connected thereto. An inflow annulus is defined at the proximal end of the bioprosthesis and an outflow annulus is defined at the distal end thereof. The porcine coronary arteries are cut away from the aortic portion of the bioprosthesis, thereby forming coronary openings in the bioprosthesis. Woven polyester cloth is sewn around the inflow annulus of the bioprosthesis to facilitate suturing of the proximal end of the bioprosthesis to a surgically prepared endogenous aortic valve root of the recipient patient. Thereafter, in cases wherein the entire bioprosthesis is implanted the distal end of the bioprosthesis may be anastomosed to the patient's aorta, and the coronary openings of the bioprosthesis are aligned with, and sutured to, the patient's coronary ostia.

In an alternative implantation procedure, the surgeon may elect to trim or cut away the distal portion of the cylindrical prosthesis body (e.g., that portion above the valve leaflets), and to implant only the proximal portion of the bioprosthesis. In such modified "partial" implantation procedure, it is unnecessary for the surgeon to anastomose that distal end of the distal end of the bioprosthesis and/or the coronary openings to the patient's aorta because such distal portions of the bioprosthesis have been trimmed or cut away prior to its implantation.

The above-described stentless aortic bioprosthesis of U.S. Pat. No. 5,197,979 (Quintero, et al.) was provided with a holding fixture which was attached to the outflow (i.e., distal) end of the bioprosthesis. An elongate handle was connectable to the holding fixture. Such handle was intended to be grasped and manipulated by the surgeon to maneuver the stentless aortic bioprosthesis to its desired implantation position. Certain problems or shortcomings were, however, associated with this holding fixture attached to the outflow (i.e., distal) end of the bioprosthesis. First, the holding fixture was of a configuration which tended to substantially block the outflow end of the prosthetic valve root cylinder, thereby preventing the surgeon from visualizing the valve leaflets from a distal vantage point, during the implantation procedure. Second, because the holding fixture was attached only to the outflow (i.e., distal) end of the stentless bioprosthesis, the exertion of forward pressure against the holding fixture tended to cause the cylindrical body and/or leaflets of the stentless bioprosthesis to compressively deform or buckle, due to the pliable or flexible nature of such stentless bioprosthesis. Such buckling or deformation of the stentless bioprosthesis could be problematic if one were to attempt, in accordance with standard operative technique, to advance the stentless bioprosthesis over a series of pre-placed suture threads which have been passed through the inflow annulus at the inflow (i.e., proximal) end of the bioprosthesis.

In view of the above-described problems associated with the prior art holding fixtures used in conjunction with stentless bioprosthesis, it is desirable to develop an improved holding apparatus which is attachable to the inflow annulus located at the inflow (i.e., proximal) end of the bioprosthesis such that, when proximally directed pressure is exerted against the holding apparatus, such pressure will be transferred through the holding apparatus so as to effect a "pulling" action upon the inflow annulus at the inflow (i.e., proximal) end of the bioprosthesis, rather than a "pushing" action upon the outflow (i.e., distal) end of the bioprosthesis. Furthermore, it is desirable for such improved holding apparatus to be configured and constructed in a manner which does not substantially block the outflow opening at the outflow (i.e., distal) end of the bioprosthesis, thereby allowing the surgeon to clearly view and properly orient the valve leaflets and commissurae of the bioprosthesis during the implantation procedure. Also, it is desirable that the holding apparatus be constructed in a manner which firmly holds the stentless bioprosthesis during any trimming or cutting away of the distal portion of the bioprosthesis, as is sometimes done in the modified or partial implantation technique described hereabove.

SUMMARY OF THE INVENTION

In general, the present invention provides a prosthetic heart valve holding apparatus which comprises a cage or enclosure which substantially surrounds a prosthetic heart valve, and which is releasably attachable to the proximal end of the prosthetic heart valve. A handle may be attachable to the holding apparatus to facilitate advancement of the heart valve to its desired implantation site. Because the cage or enclosure of the holding apparatus is attached to the prosthetic heart valve at or near its proximal end, the exertion of forwardly directed advancement force upon the holding apparatus (e.g., by pushing on a handle attached to the holding apparatus ) will be converted into a "pulling" force on the proximal portion of the prosthesis rather than a "pushing" force on the distal end thereof.

In accordance with the invention, the holding apparatus may generally comprise a) a distal hub member and b) a plurality of strut members which extend downwardly from said distal hub member at spaced-apart locations around. The downwardly extending strut members define a prosthetic heart valve receiving space beneath the distal hub member and inboard of the strut members. A bioprosthetic heart valve (e.g., a stentless bioprosthesis) having an annular sewing ring (e.g., a dacron mesh ring) at its proximal end is insertable within the receiving space such that the bottom ends of the strut members may be connected or attached to or immediately above the sewing ring, at the proximal end of the prosthesis. A handle may be formed upon, or may be attachable to, the distal hub member of the holding apparatus such that the handle extends upwardly therefrom. A surgeon may then grasp the handle, and may utilize the handle to advance the holding apparatus (with the heart valve prosthesis releasably mounted therewithin) to the intended implantation site. Because the holding apparatus is connected at or near the proximal (inflow) end of the prosthesis, the exertion of pushing force on the handle will cause a "pulling" force to be applied to the proximal (inflow) end of the prosthesis rather than exerting a "pushing" force against the distal (outflow) end of the prosthesis. In this manner, the holding apparatus allows the bioprosthesis to be advanced into position without compressively deforming or collapsing the prosthesis, and without any need for use of extraneous instruments (e.g., forceps) to grasp and pull the proximal (inflow) end of the bioprosthesis into place. After the proximal (inflow) end of the bioprosthesis has been positioned immediately adjacent the endogenous valve root or other intended site of implantation, sutures may be tied in place to affix the sewing ring at the proximal (inflow) end of the prosthesis to the endogenous valve root or other host tissue. Thereafter, the prosthesis is disconnected and detached from the holding apparatus, and the holding apparatus is extracted and removed thereby removing the bioprosthesis in its implanted position within the host body.

Further in accordance with the invention, a proximal ring member may be formed at the proximal end of the holding apparatus, and sutures or other releasable connections may be formed directly between the proximal ring member of the holding apparatus and the proximal (inflow) end of the prosthesis. In this manner, the proximal ring member formed on the holding apparatus will serve to rigidly maintain the proximal (inflow) end of the prosthesis in a rigidly fixed open configuration during placement of the sutures through the sewing ring of the prosthetic valve, and throughout the implantation procedure. The surgeon may then effectively suture the proximal mesh ring of the prosthesis (e.g., the portion which protrudes below the proximal ring member of the holding apparatus (to the body of the patient) while the proximal ring member of the holding apparatus holds the proximal (inflow) opening of the prosthesis in it's intended open configuration. Additionally, when the holding apparatus is being used in conjunction with a stentless aortic bioprosthesis or other aortic valve prosthesis of the type having openings which are intended to be sutured to the aortic tissue of the patient about the coronary ostia, it may be desirable to provide a proximal ring member on the holding apparatus which is transectable or severable into a plurality of segments. In this manner, the bioprosthesis may be sutured or otherwise affixed to the coronary ostia of the patent before detachment and removal of the holding apparatus is accomplished, and the gaps or openings which exist between separate segments of the inferior ring member may be utilized as passageways through which the sutured interconnection between the bioprosthesis and the coronary artery of the patient may pass. This will permit the holding apparatus to be extracted and removed from the patient even after the bioprosthesis has been securely sutured to the coronary ostia of the patient. The openings which are created by segmenting of the proximal ring member may be utilized as passageways through which the previously-created interconnections between the bioprosthesis and the body of the patient may pass. This allows the holding apparatus to be extracted and removed after the aortic bioprosthesis contained therewithin has been suture or otherwise affixed to the coronary ostia of the patient.

Still further in accordance with the invention, the holding apparatus operates to rigidly support and hold the proximal end of the bioprosthesis in a fully opened, non-disfigured condition during the implantation procedure. This aspect of the invention is particularly prominent in embodiments which incorporate the above-described proximal ring member which is literally attached fully around the proximal end of the bioprosthesis. By rigidly holding and supporting the bioprosthesis in its desired, open, non-disfigured condition the holding apparatus of the present invention serves to prevent the phenomenon of multiple plications during implantation of the stentless bioprosthesis. By rigidly supporting and holding the proximal end of the bioprosthesis, the holding apparatus allows the surgeon to apply pressure to the sewing ring portion of the bioprosthesis during passage of sutures and implantation of the bioprosthesis without forming unwanted folds, plications, indentations or invaginations in the bioprosthesis. This ensures that, when finally implanted, the bioprosthesis will be in its desired non-deformed configuration, thereby providing for optimal functionality of the bioprosthesis after implantation.

Still further in accordance with the invention, the holding apparatus may be releasably connected to the bioprosthesis contained therewithin by any suitable type of releasible connecting member, apparatus, or substance. For example, the bioprosthesis may be releasably connected to the holding apparatus by way of suture thread(s), clasp(s), clip(s), clamp (s), hook(s), strap(s), ligature(s), adhesive(s), magnet(s), etc. In the preferred embodiment described herebelow, suture threads are utilized to releasably attach the bioprosthesis to the holding apparatus. Such suture threads are passed through apertures or holes formed at various locations on the holding apparatus, and are stitched through the body of the bioprosthesis such that the proximal (inflow) end of the bioprosthesis is attached to the proximal end of the holding apparatus, and further such that several points adjacent the distal end of the bioprosthesis are also attached to adjacent distal locations on the holding apparatus. These suture threads are strung over adjacent locations on the holding apparatus, such adjacent locations being readably accessible during the implantation procedure to permit the surgeon to cut or sever the suture threads at such locations. Such cutting or severing of the suture threads serves to release the bioprosthesis from the holding apparatus, thereby allowing the holding apparatus to be extracted and removed.

Still further in accordance with the invention, the holding apparatus may incorporate one or more hinges or bendable regions which permit flexing or relaxation of the functional shape of the holding apparatus to facilitate its intended use, extraction and removal.

Still further in accordance with the invention, the holding apparatus may be constructed such that open areas are formed about the lateral sides of the bioprosthesis to permit the surgeon to optionally trim or cut away the distal portion of the bioprosthesis in cases wherein the surgeon has elected to perform a modified "partial" bioprosthesis implantation procedure. In this regard, suture threads or other markings may be formed on the bioprosthesis to mark a line above the distal-most location(s) of the valve leaflets so that the surgeon may safely cut away that portion of the bioprosthesis which extends above such suture threads or other markings, without damaging the valve leaflets and without impairing the hemodynamic valving capability of the bioprosthesis.

Still further in accordance with the present invention, the holding apparatus may comprise a hub member positionable adjacent the distal end of the prosthesis body, and a plurality of elongate strut members having proximal ends and distal ends which are attached to the hub members such that the strut members extend substantially downward therefrom so as to define a hollow prosthesis retention space inboard of the strut members and beneath the hub member. Disposed on the proximal end of the strut members is an attachment ring for maintaining the prosthesis within the retention space. The proximal inflow end of the prosthesis is releasably connected to the attachment ring to allow the holding apparatus to be selectively disengaged from the prosthesis.

The attachment ring itself preferably comprises an inner ring member which is attached to the proximal ends of the strut members, and an outer ring member which is releasably attached to the inner ring member. In this respect, a portion of the prosthesis is frictionally captured between the inner and outer ring members. The application of a force in a distal direction to the hub member subsequent to the detachment of the inner ring member from the outer ring member facilitates the distal movement of the inner ring member relative to the outer ring member, thereby resulting in the separation of the inner and outer ring members from each other and the release of the portion of the prosthesis from therebetween.

The inner and outer ring members of the attachment ring are releasably attached to each other by at least one suture thread extending therebetween. In this respect, the inner and outer ring members each include at least one pair of suture passage apertures formed therein, with the suture passage apertures of one pair being coaxially aligned with respective ones of the suture passage apertures of the other pair for allowing the suture thread to be extended between the inner and outer ring members. Additionally, the inner and outer ring members each preferably include at least one enlarged attachment region formed thereon, with each pair of suture passage apertures being formed within a respective attachment region. The attachment region formed on the inner ring member preferably includes a cutting instrument receiving notch formed therein which is sized and configured to permit a cutting instrument to be inserted thereinto for purposes of cutting the suture thread.

The inner ring member of the attachment ring defines a beveled outer surface portion, with the outer ring member defining a beveled inner surface portion having a configuration which is complementary to the outer surface portion of the inner ring member. In this respect, the portion of the prosthesis is frictionally captured between the outer and inner surface portions when the inner and outer ring members are releasably attached to each other. Additionally, the outer ring member of the attachment ring preferably includes at least one tab portion extending distally therefrom which is sized and configured to engage the inner ring member subsequent to the distal movement of the inner ring member relative to the outer ring member in an amount sufficient to release the portion of the prosthesis from therebetween. The outer ring member preferably includes three (3) pairs of tab portions extending distally therefrom, with the tab portions of each pair being disposed on either side of a respective one of the three (3) strut members of the holding apparatus when the inner and outer ring members are attached to each other.

Further aspects and advantages of the invention will become apparent to those skilled in the art upon reading and understanding of the detailed descriptions of preferred embodiments set forth herebelow.

BRIEF DESCRIPTION OF THE DRAWINGS

Illustrative and presently preferred embodiments of the invention are shown in the accompanying drawings in which:

FIG. 5a is a perspective view of a bioprosthetic aortic heart valve implantation system and its packaging;

FIG. 5b is a perspective view of the system of FIG. 5a with a handle;

FIG. 5c is an enlarged perspective view of a retainer portion of the packaging of FIG. 5a;

FIG. 5d is a perspective view of the implantation system of FIG. 5a being prepared for use;

FIG. 5e is a perspective view of removal of an identification tag of the implantation system of FIG. 5a;

FIG. 5f is a perspective view of a preparation step for the implantation system of FIG. 5a;

FIG. 6a is an exploded, perspective view of a second embodiment of the bioprosthetic aortic heart valve implantation system of the present invention.

FIG. 6b is an assembled perspective view of the second embodiment of the bioprosthetic heart valve implantation system of the present invention shown in FIG. 6a.

FIG. 7 is a perspective view of a third embodiment of a bioprosthetic aortic heart valve implantation system of the present invention.

FIG. 8 is an exploded, perspective view of the third embodiment of the bioprosthetic heart valve implantation system shown in FIG. 7.

FIG. 9a is an enlarged, partial perspective view of the region 9a encircled in FIG. 7.

FIG. 9b is a cross-sectional view taken along 9b—9b of FIG. 9a, showing the attachment ring of the implantation system as releasably attached to the bioprosthetic aortic heart valve.

FIG. 9c is a cross-sectional view similar to FIG. 9b, but showing the attachment ring of the implantation system as detached from the bioprosthetic aortic heart valve.

DETAILED DESCRIPTION OF THE PREFERRED EMBODIMENTS

Figure 1:
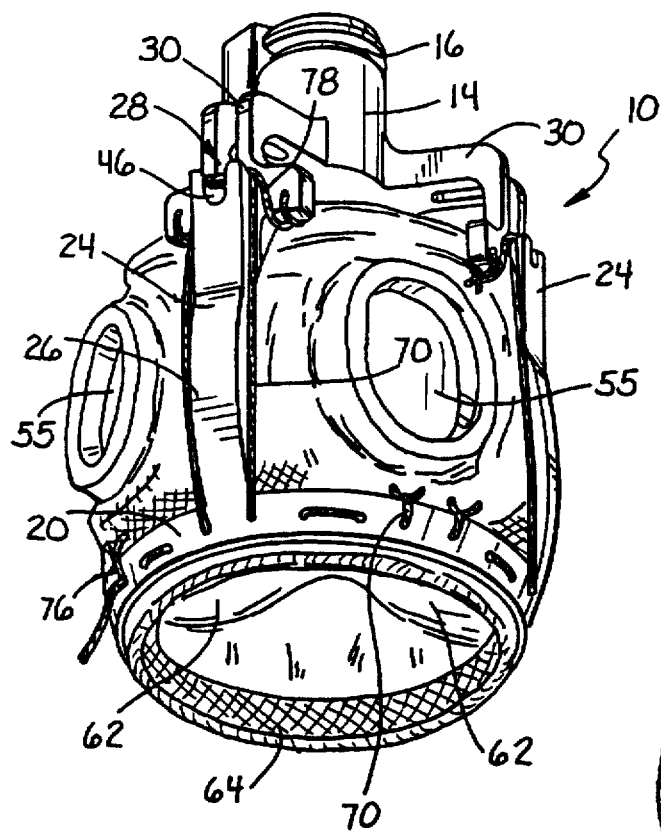
FIG. 1 is a perspective view of a first embodiment of a bioprosthetic aortic heart valve implantation system of the present invention.
Figure 2:
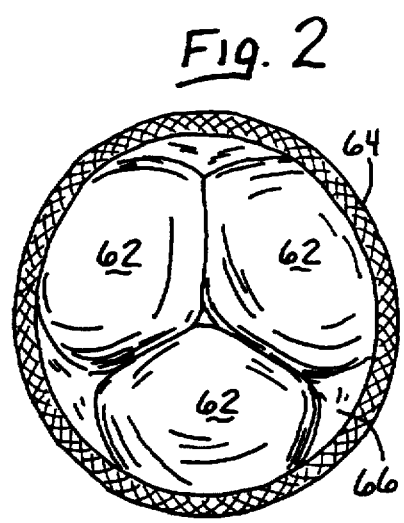
FIG. 2 is a bottom plan view of the implantation system of FIG. 1.

The accompanying figures show three (3) different embodiments of the implantation system 10, 10a, 10b of the present invention. The individual elements and aspects of these embodiments are independently combinable and interchangeable. However, it will generally be appreciated that the first embodiment shown in FIGS. 1–5 is routinely useable in procedures wherein the implantation system 10 of the present invention is detached and removed from the bioprosthetic heart valve before the body of the bioprosthesis is sutured to or otherwise connected to the coronary ostia of the patient. On the other hand, the second and third embodiments of the implantation system 10a, 10b are primarily usable in procedures wherein the implantation system 10a, 10b is permitted to remain attached to the bioprosthesis during the process of suturing or otherwise attaching the bioprosthesis to the coronary ostia, and thereafter, the implantation system 10a, 10b is detached and removed from the patient without disrupting the previously-formed anastomosis or connection between the bioprosthesis and the coronary ostia.

i. First Embodiment

FIGS. 1–5, show a first embodiment of a bioprosthetic heart valve implantation system 10 of the present invention. The implantation system 10 shown in FIG. 1–5 includes a holding apparatus 12 having a stentless bioprosthetic heart valve 54 mounted therewithin.

The preferred holding apparatus 12 comprises a distal central hub member 14 whose center is in alignment with a longitudinal axis LA of the holding apparatus 12, and an proximal ring member 20 having a series of apertures 22 formed therein, at spaced apart locations thereraround. Each aperture 22 is capable of having a suture thread passed therethrough. Although the embodiment shown in the drawings includes a total of 24 apertures 22 formed in the proximal ring member 20, the actual number of such apertures 22 may vary, and may in some embodiments number fewer than 24. Typically 18–24 of these apertures 22 will be utilized.

The preferred holding apparatus 12 has three strut members 24 which extend outwardly and downwardly (i.e., in the proximal direction) from the central hub member 14 to the ring member 20. Each of the three strut members 24 may be positioned directly opposite one of the three cusps or commissurae of the prosthetic valve. It will be appreciated, however, that the specific number of strut members 24 may not be critical to the invention, and various designs of the holding apparatus 12 may be employed wherein, as an alternative to the use of individual strut members 24, the holding apparatus body may be a cylindrical or bulbous cage or enclosure formed of solid, perforated, mesh or other suitable material, configured to substantially surround the distal end and sides of the prosthesis retention space 52.

Also, it will be appreciated that the proximal ring member 20 shown in the drawings is an optional feature. Such proximal ring member 20 serves to substantially distribute the pulling force evenly around the inflow annulus at the proximal end of the prosthesis. Various alternative embodiments of the invention may be devised which do not include such proximal ring member 20 and wherein the proximal ends of the strut members themselves, are sewn or otherwise attached to the prosthesis 54, at discrete points or locations thereraround, or the proximal end of any continuous cage or enclosure used to form the holding apparatus 12 may be releasably attached at individual, discrete locations around the inflow annulus of the prosthesis 54.

As is apparent from the figures, the diameter of the ring member 20 is preferably larger than the diameter of the distal hub member 14. In the embodiment shown, each strut member 24 is made up of a substantially vertical first segment 26 and a substantially horizontal second segment 30. The substantially vertical first segments 26 of the strut members 24 extend upwardly from the proximal ring member 20. The substantially horizontal second segment 30 of each strut member 24 extends laterally outward from the distal hub member 14.

A suture thread retainer 28 is formed on each strut member 24. Each suture thread retainer 28 incorporates a traversing notch or channel 38 within which a plurality of suture threads may be retained. A cutting instrument entrance slot 46 is formed within each strut member 24 to permit scissors and other types of suitable instruments to be inserted thereinto, for the purpose of simultaneously cutting one or more suture threads which are disposed within the channel 38.

Figure 5E:
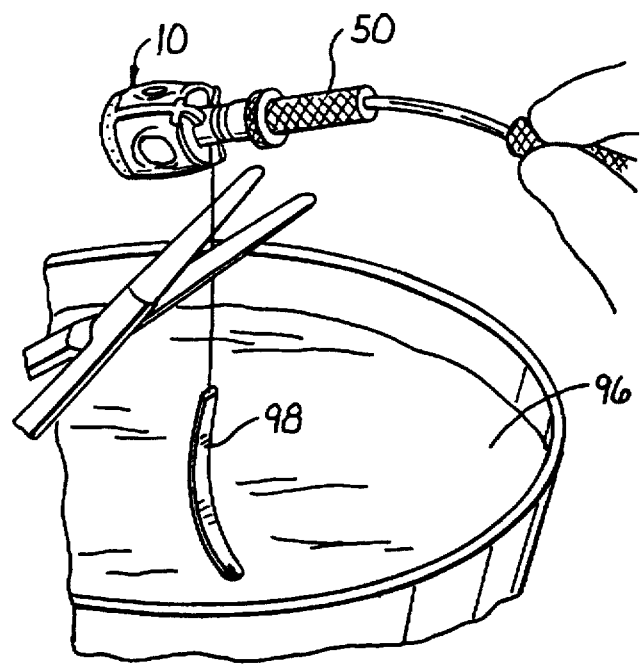
Figure 5F:
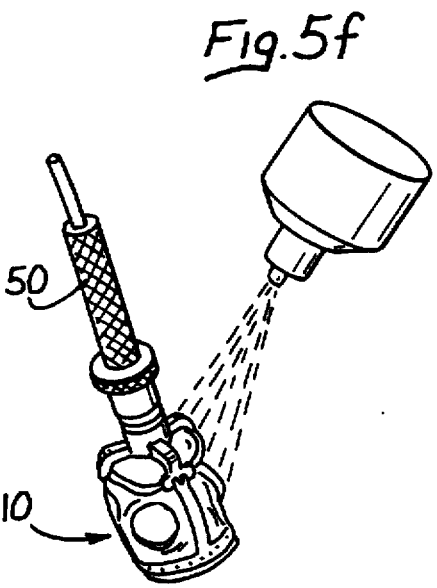
Figure 5K:
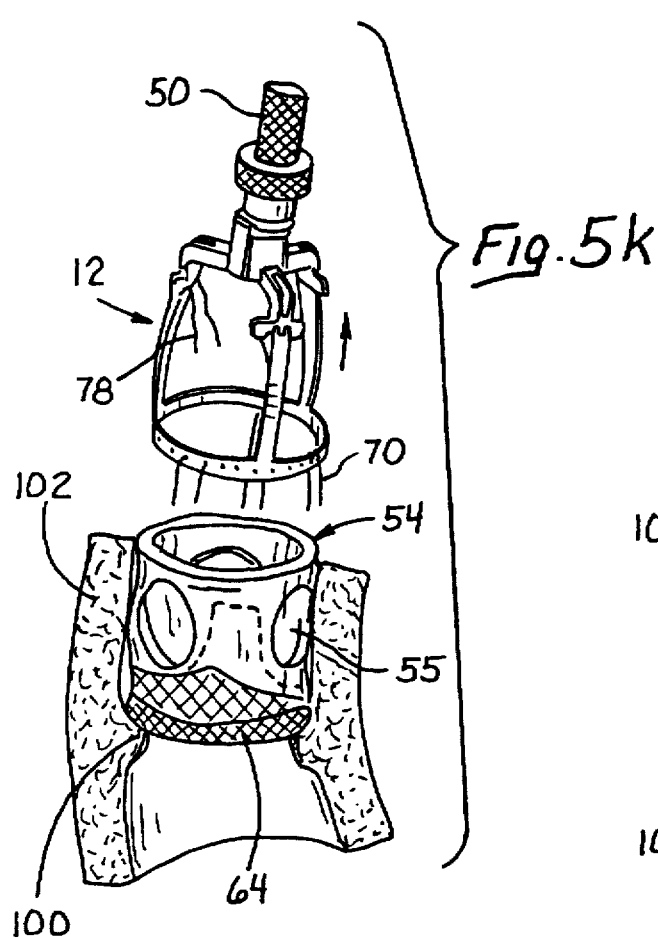
FIG. 5k is a perspective view of an implanted heart valve of the implantation system of FIG. 5a along with the holding apparatus thereof being withdrawn after valve prosthesis placement.
Figure 5H:
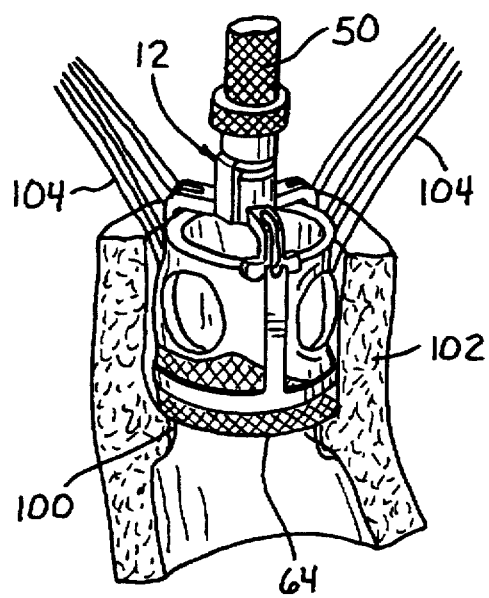
FIG. 5h is a perspective view similar to that of FIG. 5g except with the implantation system at the site of aortic root implantation.
Figure 5G:
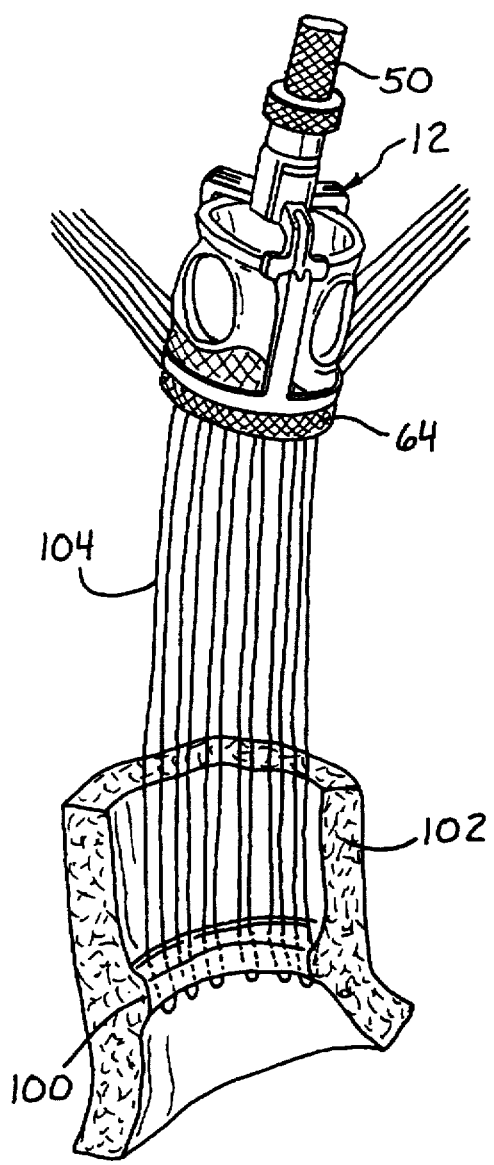
FIG. 5g is a perspective view of placed suture thread between the implantation system of FIG. 5a and an aortic root.
Figure 5J:
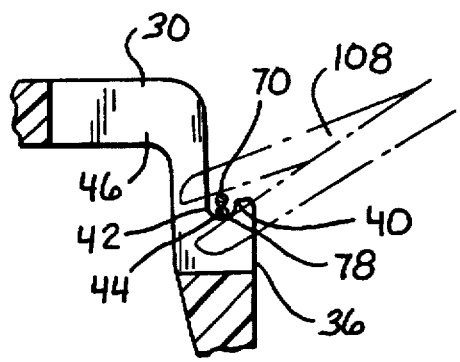
FIG. 5j is an enlarged elevation view along line 5j—5j of FIG. 5i.

As shown in significant detail of FIG. 5j, each channel 38 formed by each suture thread retainer 36 comprises an outer wall 40, an inner wall 42 and a floor 44. The manner in which the first and second suture threads 70, 78 are disposed within channels 38 is described more fully herebelow.

The distal hub member 14 is, in the embodiments shown, a generally cylindrical member having a threaded bore 48 formed therein. The threaded bore 48 is sized and configured to receive a handle member 50 (FIGS. 5b–5f). Examples of handle members 50 which may be used include handle Model 1108 or handle Model 1111 available from Baxter Healthcare Corporation, Edwards CVS Division, 17221 Red Hill Ave., P.O. Box 11150, Irvine, Calif. 92711-1150. The outer diameter of the distal hub member 14 is sufficiently small so as not to substantially block or obscure the outflow opening at the distal end of the prosthesis 54 when the prosthesis 54 is positioned within the prosthesis retention space 52 of the holding apparatus 12.

The prosthesis retention space 52 is formed between or inboard of the strut members 24 and ring member 20, and below (i.e., proximal to) the distal hub member 14. The bioprosthesis 54 is releasably mounted within the retention space 52 of the holding apparatus 12. The bioprosthesis 54 shown in the drawings is a stentless aortic bioprosthesis which comprises a cylindrical prosthesis body 56 having a plurality of valve leaflets 62 disposed therein. The outer surface of these cylindrical prosthesis body 56 may incorporate a marking thread, such as a green-colored thread, which is located immediately distal to the valve leaflets 62. This marking thread 60 will thus serve as a guide to permit optional trimming away of the distal portion of the cylindrical prosthesis body 56 without injuring the valve leaflets 62.

A ring of woven polyester mesh 64 is sewn to the inflow annulus of the prosthesis 54, and may extend beneath the proximal ring 20 of the cage, as shown. Such ring of polyester mesh material 64 facilitates suturing of the prosthesis 54 to the endogenous aortic root. An additional flap 68 of woven polyester mesh material may be sewn on a portion of the outer surface of the cylindrical prosthesis body 56, to further enhance the suture-holding of the prosthesis to specific endogenous tissue. As used herein, reference to the cylindrical body 56 of the prosthesis 54 is intended to include the polyester mesh ring 64 and polyester mesh flap 68 attached to the tissue of the prosthesis 54.

Figure 4:
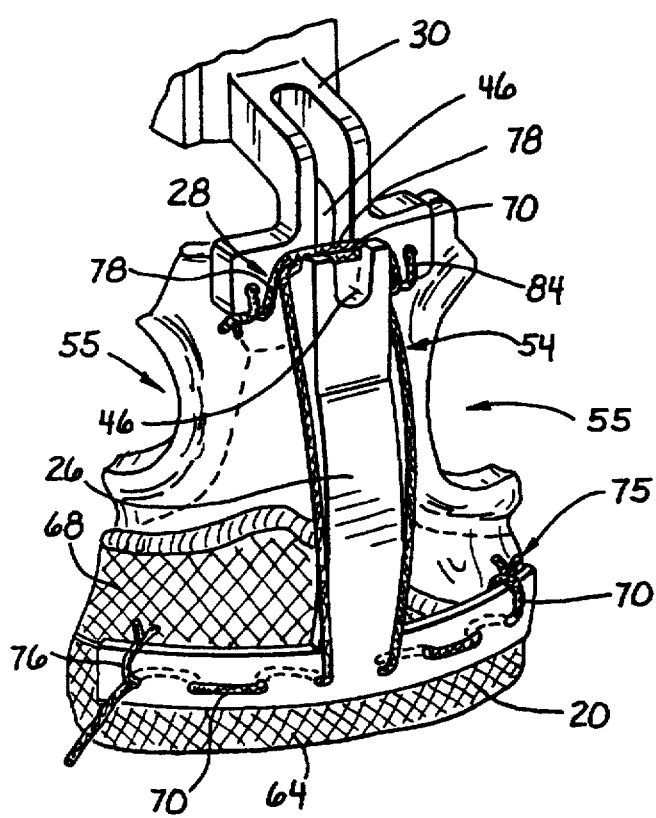
FIG. 4 is an enlarged perspective view of a portion of the implantation system of FIG. 1.
Figure 3:
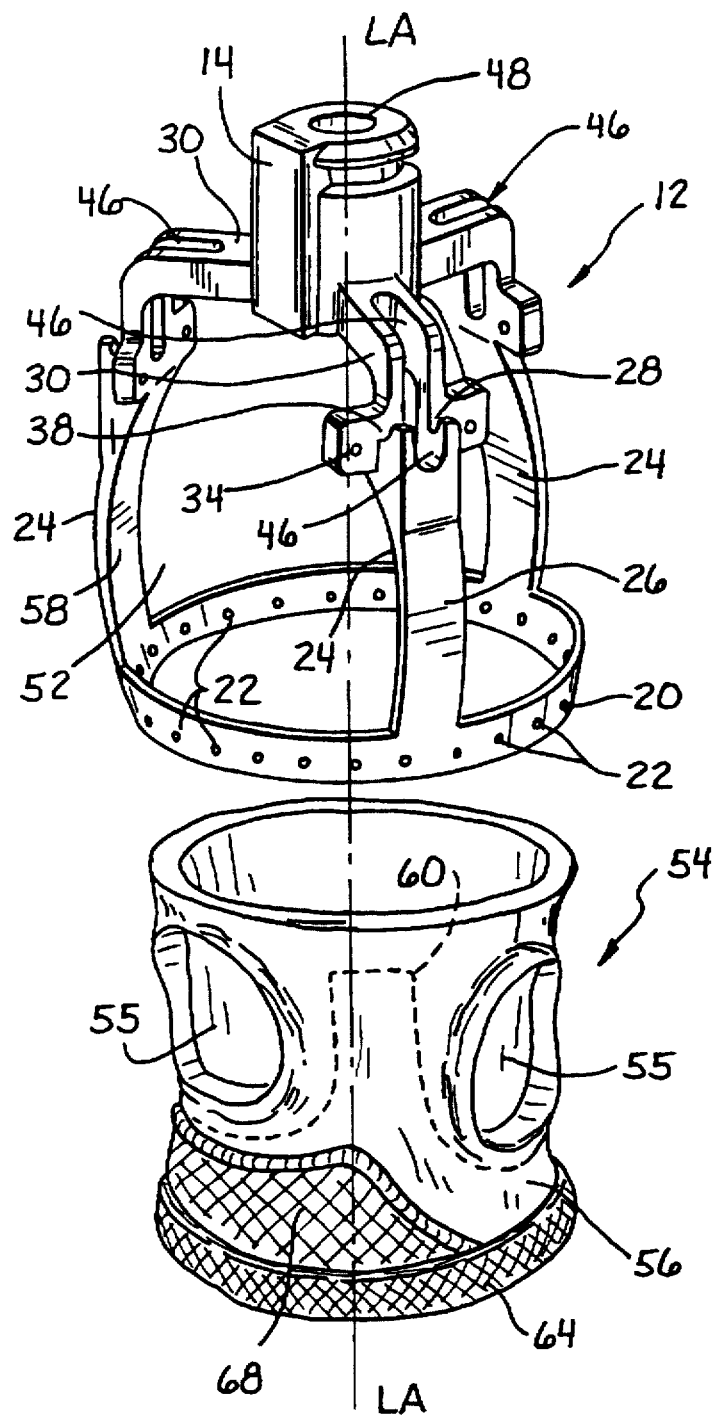
FIG. 3 is an exploded perspective view of the implantation system of FIG. 1.

The prosthesis 54 is releasably mounted within the retention space 52 by first 70 and second 78 suture threads. The specific manner in which the first 70 and second 78 suture threads are utilized to releasably attach the bioprosthesis 54 to the holding apparatus 12 can be seen from FIGS. 1 and 4. As shown, the first suture thread 70 is initially tied about the upper surface of the proximal ring member 20, immediately adjacent one of the suture package apertures 22. Thereafter, the first suture thread 70 is alternately laced in and out of the apertures 22, and is thereby passed through the under-lying cylindrical prosthesis body 56, as shown. Upon exiting the suture passage aperture 22 which is closest to each strut member 24, the first suture thread 70 is pulled upwardly, and is passed through the channel 38 of the suture thread retainer 36 formed on that strut member 24. Thereafter, the first suture thread 70 is pulled downwardly adjacent the opposite side of that strut member 24 and is then laced in and out of the previously unused suture passage apertures 22 adjacent that side of the strut member 24, to grasp the underlying cylindrical prosthesis body 56. The free end of the first suture thread 70 is then tied and knotted over the upper surface of the proximal ring member 20, in the same manner as had been done with the other end of that first suture thread 70. This is shown in FIG. 4.

The second suture thread 78 is knotted around the under-surface of the upper arm 30 of each strut member 24, and is then passed through the underlying cylindrical body 56 of the prosthesis 54, and through the channel 38 of the suture thread retainer 36, as shown, The leading end of the second suture thread 78 may optionally then be again passed through the underlying cylindrical body 56 of the prosthesis 54 a second time, and will thereafter be passed through the adjacent suture passage aperture 34 and tied beneath the undersurface of the upper arm 30 of the strut member 24, as shown. In this regard, the second suture thread 78 serves to accomplish releasable attachment of the distal aspect of the bioprosthesis 52 to the holding apparatus 12.

Figure 5I:
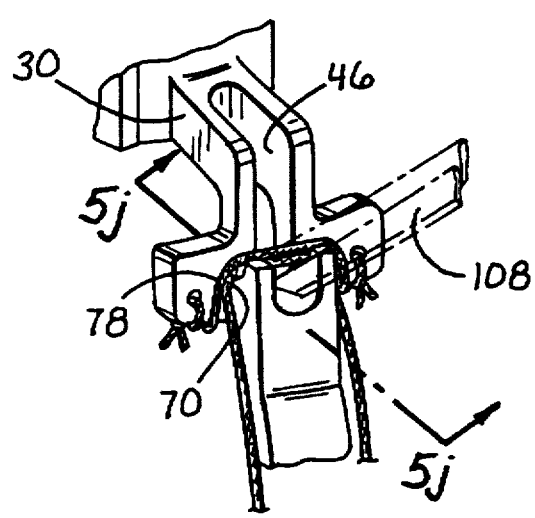
FIG. 5i is an enlarged perspective view of a portion of the system of FIG. 5a showing a suture thread retainer with suture thread therein.
Figure 10A:
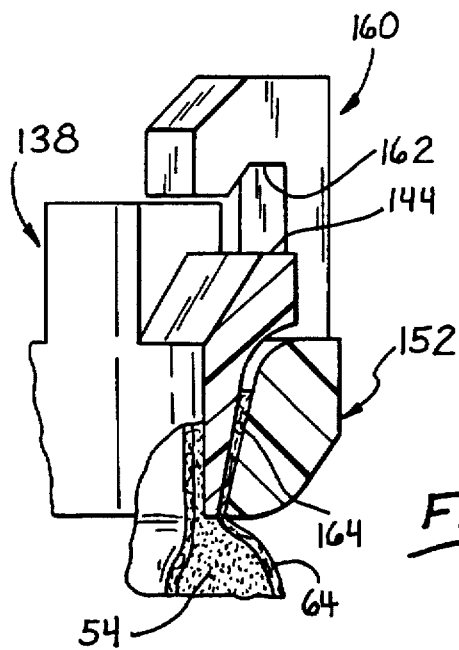
FIG. 10a is a cross-sectional view taken along line 10a—10a of FIG. 7.
Figure 10B:
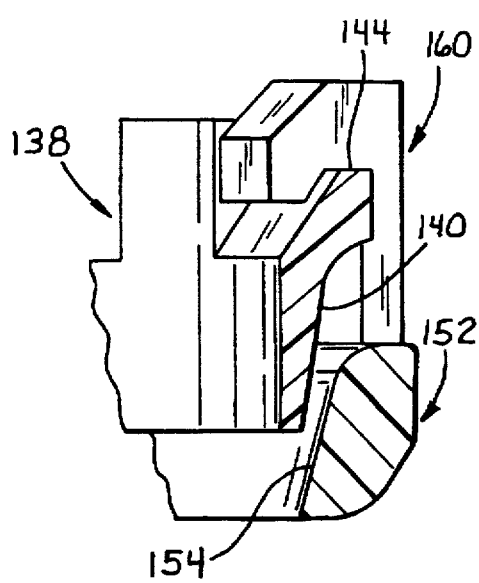
FIG. 10b is a cross-sectional view similar to FIG. 10a, but showing the attachment ring of the implantation system as detached from the bioprosthetic aortic heart valve.
Figure 11A:
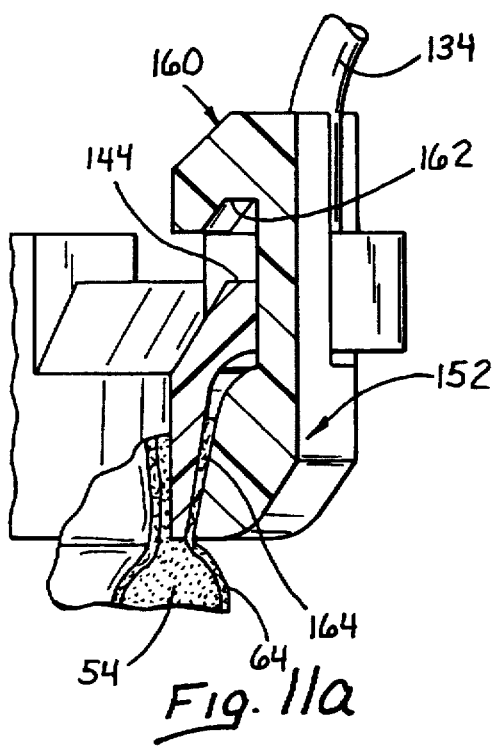
FIG. 11a is a cross-sectional view taken along line 11a—11a of FIG. 7.
Figure 11B:
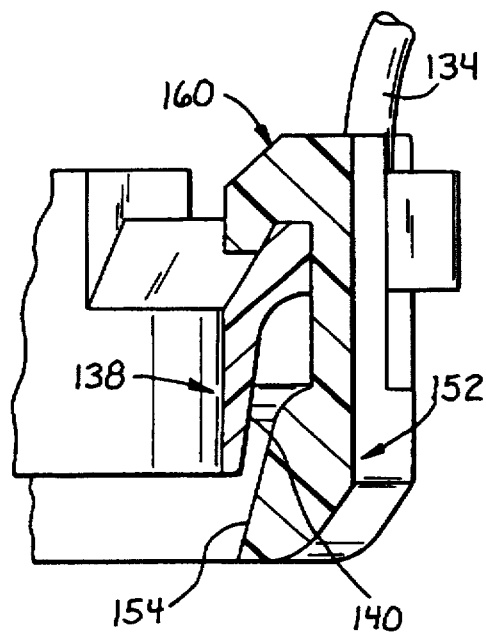
FIG. 11b is a cross-sectional view similar to FIG. 11a, but showing the attachment ring of the implantation system as detached from the bioprosthetic aortic heart valve.

The specific manner in which the first suture thread 70 and second suture thread 78 are disposed within the suture retainer 36 are shown in detail in FIG. 5i–5j. With reference to FIGS. 5i–5j it can be seen that the channel 38 formed within the suture retainer 36 is defined by an inner wall 42, a base 44, and an outer wall 40. The first suture thread 70 and second suture thread 78 are positioned within the channel 38 of the suture retainer 36 in side-by-side juxtaposition. Thus, the surgeon may insert a single cutting instrument 108, such as scissors, into the cutting instrument receiving slot 46 of each strut member 24 for the purpose of simultaneously severing both the first suture thread 70 and the second suture thread 78 associated with that particular strut member 24. In this regard, only three cutting operations are necessary to effectively sever all three of the first suture threads 70 and all three of the second suture threads 78, thereby releasing the bioprosthesis 54 from its attachment to the holding apparatus 12.

The preferred methodology by which the first embodiment of the implantation system 10 may be utilized to facilitate surgical implantation of the bioprosthesis 54 is shown in FIGS. 5a–5j. With reference to FIGS. 5a–5j, the implantation system 10 is packaged as shown in FIG. 5a in a sterile plastic jar 86 with a plastic retainer 88 having a tab 90. The jar 86 contains buffered glutaraldehyde 92. A gloved hand 93 is used to remove the system 10 from the jar 86 by grasping the tab 90 of the retainer 88. The retainer 88 has a track 94 which releasably retains the hub member 14 by engaging a groove 16 thereof. Once the implantation system 10 is removed from the jar 86, the handle member 50 is threaded into the threaded bore 48 of the hub member 14. The handle member 50 is then grasped and, as shown in FIG.

5c, the retainer 88 is discarded. The valve prosthesis 54 housed within the prosthesis retention space 52 is rinsed in several fresh sterile saline solutions 96 as known in the art and exemplified in FIG. 5d, and its identification tag 98 is removed as shown in FIG. 5e and retained for record keeping. To prevent drying of the prosthesis 54 prior to implantation, sterile saline may be applied, as illustrated in FIG. 5f, every one to two minutes until implantation.

FIGS. 5g–5h show one method of initially positioning and securing the inflow annulus of the prosthesis 54 at a supra-annular implantation site immediately above the endogenous aortic root 100. As shown, the bioprosthesis 54, while it remains releasably mounted within the holding apparatus 12 is positioned at an exteriorized location immediately above the upper scissor receiving notch 102. Suture threads 104 are passed through the polyester mesh ring 64 sewn to the inflow annulus of the prosthesis 54, through the endogenous aortic root 100, and again upwardly through the polyester mesh ring 64. After such suture threads 104 have been installed all the way around the endogenous aortic root 100 and the prosthesis 54, proximally directed pressure is applied to the handle 50, so as to advance the holding apparatus 12 and the prosthesis 54 downwardly over the pre-positioned suture threads 104, to a point (FIG. 5h) where the inflow annulus of the prosthesis 54 is in its desired supra annular position immediately above the endogenous aortic root 100.

Thereafter, as shown in FIG. 5i–5j, scissors 108 will be inserted into each of the cutting instrument receiving slots 46, and will be utilized to simultaneously cut the first 70 and second 78 suture threads extending through the channel 38 of the suture retainers 36 formed on each strut member 24. In this regard, only three scissor snips will be required to effect cutting of all three first suture threads 70 as well as all three second suture threads 78. Because both ends of each first suture thread 70, and both ends of each second suture thread 78, are tied and anchored to the holding apparatus 12, the subsequent extraction and pulling away of the holding apparatus 12 will also serve to draw the first suture threads 70 and second suture thread 78 out of the prosthesis 54. In this regard, the severed first suture thread 70 and second suture thread 78 will be withdrawn and carried away with the used holding apparatus 12, as shown in FIG. 5k.

After the holding apparatus 12 has been removed and discarded, the surgeon may tie and cut away excess quantities of the suture threads 104, and may effect any additional suturing required to secure the distal end of the prosthesis 54 and/or the coronary openings 55 to the patient's coronary ostia.

ii. Second Embodiment

Figure 6C:
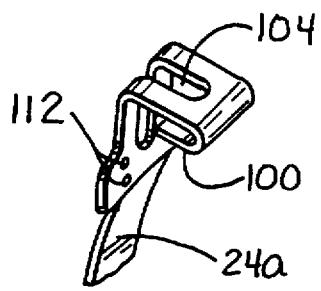
FIG. 6c is an enlarged perspective showing of the upper end of one of the strut members of the apparatus of FIG. 6a, wherein a tab formed on the upper end of the strut member has been bent over to facilitate attachment of the strut member to the distal hub of the apparatus.

In the second embodiment of the holding apparatus 12a, as shown in FIGS. 6a–6c, the proximal ring members 20a is segmented or divided into a plurality of separate portions. The vertical strut members 24a are capable of being splayed or bent outwardly in directions which are generally divergent from one another, so as to cause the individual segments or portions of the proximal ring member 20a to spread apart from one another. This results in the formation of gaps or openings in the proximal ring member 20a, so as to allow the proximal ring member 20a to be extracted from the patient even after the bioprosthesis contained within the holding apparatus 12a has been sutured to the coronary ostia of the patient.

More specifically, the second embodiment of the holding apparatus 12a may be constructed as a single molded piece, or alternately may be fabricated from a plurality of individual components as is specifically illustrated in the exploded view of FIG. 6a. With reference to FIG. 6a, the individual components of which the holding apparatus 12a is formed comprise a central hub member 14a and three (3) strut members 24a having respective segments of the proximal ring member 20a formed on the basal or proximal end thereof.

In the embodiment shown, the central hub member 14a is provided with three outwardly extending attachment legs 90 each such attachment leg 90 has a substantially horizontal, planar central portion 92 with vertical flanges or lips 90 formed on either side thereof. Scissor-receiving notches or cut-away areas 96 extend inwardly into each of the horizontal flat center portions 92 of the attachment legs 90.

Pass-through slots 97 are formed in each of the attachment legs 90, inboard of each horizontal flat central portions 92. Corresponding bendable tab members 100 are formed on the upper ends of the strut members 24a, and such tab members 100 are passable downwardly through the pass-through slots 97 of the attachment legs 90. Thereafter, such tab members 100 may be bent upwardly such that they abut against the under surface of the horizontal flat portion 92 of each attachment leg 90. This effectively and firmly attaches each strut member 24a to the central hub member 14a.

Separate upper scissor receiving notches 102, 104 are formed in the upper ends of the strut members 24a. As the tab members 100 are bent over, each of these upper scissor receiving notches 102, 104 becomes aligned with the corresponding notch 96 formed in the adjacent attachment leg 90 of the central hub member 14a, to facilitate insertion of scissors or other cutting instruments to sever the upper suture thread 116 passed through suture passage apertures 112 or other attachment member or apparatus by which the upper end of each strut member 24a is attached to the bioprosthesis 54 positioned within the prosthesis retention space 52a holding apparatus 12a. The preferred manner in which such upper suture threads 116 are deployed and positioned is shown in detail in FIG. 6, and is more fully described herebelow.

Each of the three (3) segments of the proximal ring member 20a shown in FIG. 6a have ends 110 which are abutable against one another such that the proximal ring member 20a will assume the assembled shape of a substantially round or circular ring. Locator projections 113 extend from some of the segment ends 110 of the proximal ring member 20a to assist in guiding and locating the ends 110 into direct abutment to form the desired ring structure.

As shown in FIG. 6, individual lower suture threads 120 may be utilized to secure the assembled proximal ring member 20a to a bioprosthesis 54 contained within the interior prosthesis receiving space 52a of such holding apparatus 12a.

In this regard, discrete groups of suture passage apertures 112 are located at specific locations on the holding apparatus 12a to facilitate releasible attachment of the holding apparatus 12a to a bioprosthesis which is positioned within the prosthesis retention space 52a of the holding apparatus 12a.

Preferably, a group of four (4) suture passage apertures 112 is formed in a substantially rectangular array near the upper end of each strut member 24a, at a location immediately adjacent the basal end of each upper scissor-receiving notch 102. In this manner, the upper suture threads 116 may be tied or otherwise anchored to the strut members 24a, and passed alternately in and out of the four (4) suture passage apertures 112, as shown in FIG. 6b, to thereby stitch or couple the upper end of each strut member 24a to a bioprosthesis 54 contained within the prosthesis retention space 52a. When it is desired to disconnect the bioprosthesis from the holding apparatus 12a, scissors may be inserted downwardly into the upper scissor receiving notches 102, so as to cut the upper suture thread 116, thereby releasing the bioprosthesis from the upper ends of the strut members 24a.

Similarly, groups consisting of four (4) suture passage apertures 112 are formed at spaced-apart locations around the proximal ring member 20a, and individual lower suture threads 120 may be tied or otherwise anchored to the suture passage aperture 112, and may be passed alternately in and out of the adjacent four (4) suture passage apertures 112 to stitch the bioprosthesis 54 within the retention space 52a to the proximal ring member 20a, as shown in FIG. 6b. Because the lower scissor receiving notches 118 extend downwardly into the upper edges of the proximal ring member 20a, at the locations between the suture passage apertures 112 of a discrete group, the tip of a pair of scissors or other cutting instrument may be inserted into each such scissor receiving notch 118 to cut each lower suture thread 120 by which the proximal ring member 20a is attached to the proximal end of the bioprosthesis. In this regard, six separate scissor snips may be utilized to completely severe all of the individual lower 120 suture threads 120 which attach the proximal ring member 20a to the proximal end of the bioprosthesis 54.

As with the first embodiment of the invention shown in FIGS. 1–5, the bioprosthesis 54 is positioned within the prosthesis retention space 52a of the holding apparatus 12a such that the proximal mesh ring 64 of the bioprosthesis 54 protrudes below the lower edge of the proximal ring member 20a. Such mounting of the bioprosthesis 54 within the retention space 52a is preferably accomplished prior to packaging within a storage container 86, as shown in FIG. 5a. This enables the surgeon to easily use the holding apparatus 12a to facilitate proper placement and suturing of the proximal sewing ring 64 of the bioprosthesis 54 to the patient prior to release or removal of the holding apparatus 12a.

In operation, the second embodiment of the holding apparatus 12a shown in FIGS. 6a–6c operates in substantially the same way as described hereabove with respect to the first embodiment shown in FIGS. 1–5. However, the second embodiment of the holding apparatus 12a has the added capability of being removed after the coronary openings 55 (see FIG. 3) of the bioprosthesis 54 have been anastomosed or otherwise attached to the coronary ostia of the patient. For example, after the holding apparatus 12a of the second embodiment (along with a bioprosthesis 54 mounted within its prosthesis retention space 52a) has been advanced to a point where the proximal mesh ring 64 of the bioprosthesis is located at its intended implantation site (e.g., the aortic annular or supra-annular position) and sutured in place, the surgeon may then proceed to suture, or otherwise attach the peripheries of the coronary openings 55 of the bioprosthesis to the aortic tissue surrounding the coronary ostia of the patient. Thereafter, scissors are inserted downwardly into the upper scissor receiving notches 102 and may be utilized to cut the upper suture thread 116, thereby enabling the upper suture thread 116 to be pulled through the body of the prosthesis such that the holding apparatus may be extracted and removed from the prosthesis. Also, scissors are inserted downwardly into each of the lower scissor receiving notches 118 formed in the proximal ring member 20a, and will be utilized to cut each of the lower suture thread 120, thereby enabling the lower suture thread 120 to be pulled through and removed from the body of the prosthesis as the holding apparatus 12a is extracted and removed.

After all of the upper suture threads 116 and lower suture threads 120 have been cut, the surgeon will splay or outwardly bend the strut members 24a away from one another so as to cause the ends 110 of the proximal ring member 20a segments to separate or part from one another. This creates gaps or openings between the adjacent ends 110 of the separate segments of the proximal ring member 20a. After such gaps or openings have been created in the proximal ring member 20a, the surgeon will lift upwardly on a handle which is attached to the central opening 48a of the central hub member 14a, thereby lifting the entire holding apparatus 12a upwardly. Such upward lifting of the holding apparatus 12a causes the previously severed upper suture threads 116 and lower suture threads 120 to be drawn or pulled through the adjacent tissue of the prosthesis, thereby freeing the holding apparatus 12a. Furthermore, as the holding apparatus 12a is lifted upwardly, the points at which the prosthesis are connected to the aortic tissue surrounding the coronary ostia will pass through the gaps or openings created between the adjacent ends 110 of separate segments of the proximal ring member 20a. In this manner, the holding apparatus 12a is extracted and removed from the body of the patient while the bioprosthesis remains in its implanted position with the coronary openings 55 of the bioprosthesis 54 being anastomosed or otherwise attached to the patient.

iii. Third Embodiment

Referring now to FIGS. 7–11b, there is depicted a holding apparatus 12b constructed in accordance with a third embodiment of the present invention. As shown in FIG. 7, the holding apparatus 12b includes the stentless bioprosthetic heart valve or prosthesis 54 mounted therewithin.

Such mounting of the prosthesis 54 within the holding apparatus 12b is preferably accomplished prior to packaging of the bioprosthesis 54 within a storage solution 92, as shown in FIG. 5a. As in the holding apparatus 12, 12a constructed in accordance with the first and second embodiments of the present invention, the holding apparatus 12b includes a central hub member 14b. The hub member 14b itself includes a female retention bore 130 formed therein to facilitate the attachment of the previously described handle member 50 to the holding apparatus 12b. Extending radially outward from the hub member 14b in equidistantly spaced intervals of approximately 120 degrees are three (3) identically configured attachment legs 132.

In addition to the hub member 14b and integral attachment legs 132, the holding apparatus 12b includes three (3) elongate strut members 134 having distal ends which are attached to the outermost ends of respective ones of the attachment legs 132. As best seen in FIG. 8, the strut members 134 may define arcuately contoured, outwardly bowed central portions. The strut members 134 extend substantially downward from the attachment legs 132 so as to define a hollow prosthesis retention space inboard of the strut members 134 and beneath the hub member 14b. As seen in FIG. 7, this retention space is sized and configured to accommodate the prosthesis 54.

The holding apparatus 12b of the third embodiment further comprises an attachment ring 136 which is disposed on the proximal ends of the strut members 134 for maintaining the prosthesis 54 within the retention space defined within the holding apparatus 12b. As will be discussed in more detail below, the proximal inflow end of the prosthesis 54 is releasably connected to the attachment ring 136 in a manner allowing the holding apparatus 12b to be selectively disengaged from the prosthesis 54 subsequent to the placement thereof into a desired site.

In the third embodiment, the attachment ring 136 itself comprises an inner ring member 138 which is attached to the proximal ends of the strut members 134. The inner ring member 138 includes a lower, beveled outer surface portion 140 and an upper, beveled inner surface portion 142 which defines the top rim 144 of the inner ring member 138. Formed on the top rim 144 of the inner ring member 138 are three (3) attachment lugs 146 which are used to facilitate the attachment of the proximal ends of the strut members 134 to the inner ring member 138. As such, the attachment lugs 146 are oriented about the periphery of the top rim 144 in equidistantly spaced intervals of approximately 120 degrees.

In addition to the attachment lugs 146, formed on the top rim 144 of the inner ring member 138 are three (3) enlarged attachment regions 148. In the third embodiment, each attachment region 148 is centrally positioned between a respective pair of the attachment lugs 146. As such, like the attachment lugs 146, the attachment regions 148 are preferably separated from each other by equidistantly spaced intervals of approximately 120 degrees. As best seen in FIG. 9a, each attachment region 148 includes a spaced pair of suture passage apertures extending therethrough which are separated by a cutting instrument receiving notch 150, the use of which will be discussed in more detail below.

In addition to the inner ring member 138, the attachment ring 136 of the holding apparatus 12b includes an outer ring member 152 which is releasably attached to the inner ring member 138. As will also be discussed in more detail below, a portion of the prosthesis 54 is frictionally captured between the outer and inner ring members 152, 138 when they are releasably attached to each other. The outer ring member 152 is adapted to receive the inner ring member 138 in a nesting fashion, and includes a beveled inner surface portion 154 having a configuration which is complementary to the outer surface portion 140 of the inner ring member 138. Additionally, as with the inner ring member 138, formed about the top edge of the outer ring member 152 in equidistantly spaced intervals of approximately 120 degrees are three (3) enlarged attachment regions 156. As best seen in FIG. 9a, extending through each of the attachment regions 156 is a spaced pair of suture passage apertures 158.

In the third embodiment, the releasable attachment of the inner and outer ring members 138, 152 to each other is facilitated by initially inserting the inner ring member 138 into the outer ring member 152 such that the attachment regions 148 of the inner ring member 138 are vertically aligned with respective ones of the attachment regions 156 of the outer ring member 152. When so aligned, the suture passage apertures of each pair disposed within a respective attachment region 148 are coaxially aligned with respective ones of the suture passage apertures 158 of the corresponding attachment region 156. As further seen in FIG. 9a, a suture thread 159 is extended through the coaxially aligned suture passage apertures of each corresponding pair of attachment regions 148, 156 to facilitate the releasable attachment of the inner and outer ring members 138, 152 to each other.

As best seen in FIGS. 7 and 8, the outer ring member 152 of the attachment ring 136 further includes three (3) spaced pairs of tab portions 160 which extend distally from the top rim thereof. Each pair of tab portions 160 is centrally positioned between a respective pair of attachment regions 156. In this respect, when the inner and outer ring members 138, 152 are releasably attached to each other in the aforementioned manner, each pair of tab portions 160 is oriented so as to receive a respective one of the attachment lugs 146 of the inner ring member 138 therebetween. As such, when the inner and outer ring members 138, 152 are releasably attached to each other, the tab portions 160 of each pair extend upwardly along either side of a respective strut member 134 of the holding apparatus 12d. Each tab portion 160 of the outer ring member 152 has a generally hook-shaped configuration, and defines a channel 162 which is directed downwardly toward the beveled inner surface portion 154 of the outer ring member 152.

Referring now to FIGS. 9b-11b, the prosthesis 54 with which the holding apparatus 12b is preferably utilized includes the layer of mesh 64 which is sewn to and extends about the inflow annulus thereof. Importantly, the mesh 64 defines an excess end portion 164 which extends along, but is not secured to, the outer surface of the prosthesis 54 adjacent the inflow annulus thereof. As previously explained, the prosthesis 54 is maintained within the retention space of the holding apparatus 12b by the releasable connection of the attachment ring 136 to the prosthesis 54. In the holding apparatus 12b, the releasable connection of the attachment ring 136 to the prosthesis 54 is facilitated by the frictional capture of the end portion 164 of the mesh 64 between the complementary beveled outer and inner surface portions 140, 154 of the inner and outer ring members 138, 152 when releasably attached to each other in the aforementioned manner. The frictional retention of the end portion 164 between the inner and outer ring members 138, 152, and in particular the outer and inner surface portions 140, 154 thereof, is shown in FIGS. 9b, 10a and 11a. When it is desired to disengage the holding apparatus 12b from the prosthesis 54 subsequent to the placement thereof in a desired site, the inner and outer ring members 138, 152 are detached from each other so as to allow the end portion 164 of the mesh 64 to be released from compression between the beveled outer and inner surface portions 140, 154.

The detachment of the inner and outer ring members 138, 152 from each other is facilitated by cutting each of the three (3) suture threads 159 extending between corresponding pairs of the attachment regions 148, 156. Such cutting is accomplished by inserting the end of a cutting instrument into the notches 150 of the attachment regions 148 in succession, and severing the suture threads 159. After the suture threads 159 have been severed by the cutting instrument, the application of force in a distal direction to the hub member 14b facilitates the distal movement of the inner ring member 138 relative to the outer ring member 152. Such distal movement results in the separation of the inner and outer ring members 138, 152 from each other, and the release of the end portion 164 from therebetween. Such distal movement of the inner ring member 138 relative to the outer ring member 152 which facilitates the release of the end portion 164 from therebetween is best shown in FIG. 9c.

As will be recognized, subsequent to the release of the end portion 164 from between the inner and outer ring members 138, 152, it is still necessary that the outer ring member 152 be withdrawn from within the operative site along with the inner ring member 138. Despite the detachment of the inner ring member 138 from the outer ring member 152 facilitated by the severing of the suture threads 159, the outer ring member 152 is pulled from the operative site by the inner ring member 138 due to the inclusion of the tab portions 160 on the outer ring member 152.

As best seen in FIGS. 10a-11b, the tab portions 160 of the outer ring member 152 engage the inner ring member 138 subsequent to the distal movement of the inner ring member 138 relative to the outer ring member 152 in an amount sufficient to release the end portion 164 of the mesh 64 from therebetween. In this respect, subsequent to such distal movement of the inner ring member 138, the top rim 144 thereof is received into the channels 162 of the tab portions 160, thus causing the continued distal movement of the inner ring member 138 to effectively draw the outer ring member 152 therewith. As a result, when the top ring 144 of the inner ring member 138 is received into the channels 162 of the tab portions 160, a sufficient gap is defined between the outer and inner surface portions 140, 154 so as to facilitate the release of the end portion 164 from therebetween. Thus, the holding apparatus 12b moves independently of the prosthesis 54.

It is to be appreciated that the invention has been described hereabove with reference to certain presently preferred embodiments and examples only, and no effort has been made to exhaustively describe all possible embodiments and examples of the invention. Indeed, various adaptations and modifications may be made to the specific embodiments described hereabove, without departing from the intended spirit and scope of the invention. Accordingly, it is intended that all reasonable modifications and alterations to the above-described embodiments and examples, be included within the scope of the following claims.

What is claimed is:

1. A holding apparatus for facilitating the surgical implantation of a heart valve prosthesis of the type having, i) a generally tubular prosthesis body having an inner surface, an outer surface, a proximal end, a distal end, an inflow annulus at the proximal end thereof, an outflow annulus at the distal end thereof, and ii) a plurality of valving members disposed within the prosthesis body to perform a hemodynamic valving function and a sewing ring attached to the inflow annulus to facilitate suturing of the inflow annulus to an endogenous opening, said holding apparatus comprising:
   a) a hub member positionable adjacent the distal end of the prosthesis body
   b) a plurality of elongate strut members having proximal ends and distal ends which are attached to said distal hub member such that the strut members extend substantially downward therefrom so as to define a hollow prosthesis retention space inboard of said strut members and beneath said hub member;
   c) at least one releasable attachment means for releasably holding the prosthesis within said prosthesis retention space such that the proximal inflow end of the prosthesis is connected to the strut members; and
   d) a proximal ring member attached to the proximal ends of said strut members, said proximal ring member being attachable about the proximal inflow annulus of the prosthesis such that, when a force is applied in the proximal direction against the distal hub member of the holding apparatus, such force will be transferred through said strut members to said proximal ring member, thereby resulting in the application of a distally directed pulling force which is annularly distributed about the proximal inflow annulus of the prosthesis.

2. The holding apparatus of claim 1, further comprising:
   an elongate handle attachable to the distal hub member of the holding apparatus, and extendable in a distal direction therefrom.

3. The holding apparatus of claim 2 wherein said distal hub member has a female retention bore formed therein and wherein said elongate handle member has a distal male member formed thereon, the distal male member of said handle being engageable within the female retention bore of the distal hub member to effect attachment of said handle to said holding apparatus.

4. The holding apparatus of claim 1 wherein:

said proximal ring member is severed at at least two locations such that said proximal ring member may be separated into a plurality of segments; and, said strut members being bendable to cause the proximal ring member to separate such that spaces are created between the segments of said ring member.

5. The holding apparatus of claim 1 further comprising:

at least one releasable attachment member for temporarily connecting the inflow annulus at the proximal end of a heart valve prosthesis disposed within said hollow prosthesis retention space, to the proximal ends of the strut members;

said releasable attachment member being manually disconnectable from said prosthesis in a manner which releases the holding apparatus from said prosthesis.

6. The holding apparatus of claim 5 wherein:

said at least one releasable attachment member comprises a suture thread anchored to the holding apparatus and passable through a prosthesis which is disposed within the hollow prosthesis retention space, to releasably attach said prosthesis to said holding apparatus;

a portion of said suture thread being located upon the holding apparatus at a first location which is sufficiently accessible during the implantation procedure to permit cutting of said suture thread at said first location, thereby causing the prosthesis to be disconnected from the holding apparatus such that the holding apparatus may be subsequently extracted and removed, leaving the heart valve prosthesis in place.

7. The holding apparatus of claim 6 wherein said holding apparatus further comprises:

a cutting instrument retention notch formed in said holding apparatus at said first location;

said cutting instrument retention notch being sized to permit a cutting instrument to be inserted thereinto for the purpose of cutting of said suture thread at said first location.

8. The holding apparatus of claim 6 wherein:

a plurality of first suture threads are connected to the proximal ends of the strut members of the holding apparatus and are passed through the inflow annulus at the proximal end of a heart valve prosthesis disposed within the hollow prosthesis retention space of the holding apparatus, to connect the distal ends of the strut members to the inflow annulus of the prosthesis; and, a plurality of second suture threads are additionally anchored to the distal hub member of the holding apparatus and are passed through the heart valve prosthesis at locations which are distal to the proximal end of the prosthesis, to effect further connection of the prosthesis to the holding apparatus;

said first suture threads and said second suture threads being passed through said first location and positioned in side-by-side juxtaposition, such that said first suture threads and said second suture threads may be concurrently severed by a cutting instrument at said first location.

9. The holding apparatus of claim 8 wherein a suture retainer is formed on each of said strut members, and wherein said first suture threads and said second suture threads are passed through said suture retainer in side-by-side juxtaposition, such that said first and second suture threads may be simultaneously cut by a single cutting action performed at the location of said suture retainer.

10. The holding apparatus of claim 9 wherein a cutting instrument receiving slot is formed in said holding apparatus, in the region of said suture retainer, to permit a cutting instrument to be inserted for the purpose of cutting said first and second suture threads at the location of said suture retainer.

11. The holding apparatus of claim 9 wherein said suture retainers are located adjacent the distal end of the holding apparatus so as to be easily accessible during the implantation procedure.

12. The holding apparatus of claim 1 wherein:

said at least one strut member comprises three strut members spaced substantially equidistant from one another.

13. The holding apparatus of claim 1 wherein:

said proximal ring member has a plurality of suture-passage apertures extending therethrough to facilitate suturing of said proximal ring member to the proximal end of a prosthesis disposed within said hollow prosthesis retention space.

14. The holding apparatus of claim 1 wherein a series of suture passage apertures are formed in said proximal ring member, on either side of each strut member, to permit a suture thread to be passed therethrough for the purpose of releasably attaching said proximal ring member to the inflow annulus of a heart valve prosthesis positioned within the prosthesis retention space of the holding apparatus.

15. The holding apparatus of claim 14 wherein 18–24 of said suture passage apertures are formed in said proximal ring member.

16. A heart valve prosthesis implantation system comprising the holding apparatus of claim 1, further in combination with a heart valve prosthesis disposed within the prosthesis retention space of said holding apparatus.

17. The system of claim 16 wherein said heart valve prosthesis is a stentless porcine bioprosthesis.

18. The system of claim 16 wherein said plurality of valving members disposed within the cylindrical prosthesis body comprise tricuspid valve leaflets.

19. The system of claim 18 wherein said heart valve prosthesis further comprises:

markers formed on said cylindrical prosthesis body, distal to said valve leaflets, to guide the optional cutting of the prosthesis body to remove a distal portion of the prosthesis body without injuring the valve leaflets.

20. A stentless aortic heart valve system incorporating the holding apparatus of claim 1, said system comprising:

a holding apparatus according to claim 1;

a stentless aortic bioprosthesis comprising a generally tubular prosthesis body having an inflow annulus at the proximal end thereof, an outflow annulus at the distal end thereof, a plurality of valving members disposed therewithin to hemodynamically valve blood passing through the tubular prosthesis body, and a mesh ring attached to the inflow annulus of the bioprosthesis;

said bioprosthesis being positioned within the prosthesis retention space of the holding apparatus, such that the mesh ring of the bioprosthesis protrudes beyond the proximal end of the holding apparatus.

21. The stentless aortic bioprosthesis system of claim 20 herein:

a proximal ring member is formed on the bottom ends of the elongate strut members of the holding apparatus, said proximal ring member having a plurality of suture passage apertures formed therein; and, at least one suture thread being passed in and out of the suture passage apertures formed in the proximal ring member of the holding apparatus and through the prosthesis body to effect releasable attachment of the proximal ring member of the holding apparatus to the prosthesis while the prosthesis is positioned within the retention space of the holding apparatus.

22. The stentless aortic bioprosthesis system of claim 21 wherein the proximal ring member of the holding apparatus is separable into a plurality of segments after it has been disconnected from the prosthesis.

23. The holding apparatus of claim 1 wherein the hub member positionable adjacent the distal end of the prosthesis body is configured so as not to block the entire outflow annulus of the bioprosthesis positioned within the holding apparatus, thereby allowing one to see the orientation of the valve leaflets by looking downwardly through the outflow annulus of the bioprosthesis.

24. The holding apparatus of claim 1 wherein said plurality of elongate strut members and said releasable attachments are attached about the bioprosthesis in such a manner as to rigidly hold the bioprosthesis in a fully open configuration, thereby deterring the formation of plications in the bioprosthesis during the implantation procedure.

25. A method for implanting a prosthetic heart valve having a generally cylindrical prosthesis body, an inflow aperture formed at a proximal end of the generally cylindrical prosthesis body, an outflow aperture formed at the distal end of the prosthesis body, a plurality of valving members disposed within the prosthesis body, and a longitudinal axis projectable longitudinally through the prosthesis body, said method comprising the steps of:

a) providing a holding apparatus which comprises a rigid holding apparatus body having a distal end, a proximal end and a hollow heart valve prosthesis retention space defined therewithin, and a releasable attachment member for releasably connecting a heart valve prosthesis mounted within the prosthesis retention space, to the holding apparatus;

b) positioning the heart valve prosthesis within the prosthesis retention space of the holding apparatus said heart valve prosthesis having a distal end and a proximal end, an outflow annulus being formed at the proximal end thereof;

c) utilizing the releasable attachment member to temporarily connect at least the proximal end of the holding apparatus to at least the proximal end of the prosthesis;

d) positioning the holding apparatus, with the heart valve prosthesis releasably mounted therewithin, a spaced distance away from an intended implantation site in the body of a patient with the proximal end of the prosthesis closest to the implantation site;

e) passing a plurality of suture threads through the intended implantation site in the body of the patient and through the inflow annulus of the heart valve prosthesis;

f) pushing the distal end of the body toward the implantation site, to advance the holding apparatus, with the heart valve prosthesis releasably mounted therein, over the previously placed suture threads, to a position where the inflow annulus of the heart valve prosthesis is in contact with the intended implantation site within the body of the patient;

g) causing the releasable connection member to release the heart valve prosthesis from its connection with the holding apparatus; and h) extracting and removing the holding apparatus, leaving the heart valve prosthesis at the intended implantation site.

26. The method of claim 25 wherein said method further comprises:

i) tying and cutting the previously placed suture threads to secure the inflow annulus of the heart valve prosthesis to the intended implantation site of the patient.

27. The method of claim 26 wherein said method further comprises the step of:

suturing the outflow aperture at the distal end of the heart valve prosthesis to the body of the patient, at a location which is downstream of the site at which the inflow aperture of the prosthesis was sutured to the body of the patient.

28. The method of claim 27 wherein the bioprosthesis has right and left coronary openings formed therein at locations which correspond to the right and left coronary ostia of the patient, and wherein the method further comprises the step of:

j) suturing the coronary openings of the prosthesis to the aortic tissue of the patient such that coronary openings of the prosthesis are in alignment with the patient's coronary ostia, thereby allowing a portion of the blood which passes out of the outflow annulus of the prosthesis to flow into the coronary arteries of the patient.

29. The method of claim 28 wherein the holding apparatus provided in step a of the method has a unitary proximal ring member which is attached to the proximal portion of the prosthesis while the prosthesis is positioned within the retention space of the holding apparatus, and wherein step h of the method is performed before step j of the method.

30. The method of claim 28 wherein the holding apparatus provided in step a has a segmented ring member which is attached by releasable connection to a proximal portion of the bioprosthesis while the bioprosthesis is positioned within the retention space of the holding apparatus, said ring member being subsequently separable into a plurality of segments such that gaps exist between said ring member segments, and wherein:

step j of the method is performed prior to step h of the method, and step h is modified to include separation of the segments of the proximal ring member, and extraction of the holding apparatus such that the sutured connection between the coronary openings of the prosthesis and the aortic tissue of the patient will remain intact and will pass through the gaps which have been created between the segments of the proximal ring member.

31. A holding apparatus for facilitating the surgical implantation of a heart valve prosthesis of the type having, i) a generally tubular prosthesis body having an inner surface, an outer surface, a proximal end, a distal end, an inflow annulus at the proximal end thereof, an outflow annulus at the distal end thereof, and ii) a plurality of valving members disposed within the prosthesis body to perform an hemodynamic valving function and a sewing ring attached to the inflow annulus to facilitate suturing of the inflow annulus to an endogenous opening, said holding apparatus comprising:

a) a hub member positionable adjacent the distal end of the prosthesis body;

b) a plurality of elongate strut members having proximal ends and distal ends which are attached to said hub member such that the strut members extend substantially downward therefrom so as to define a hollow prosthesis retention space inboard of said strut members and beneath said hub member;

c) an attachment ring disposed on the proximal ends of the strut members for maintaining the prosthesis within said prosthesis retention space, the proximal inflow end of the prosthesis being releasably connected to the attachment ring to allow the holding apparatus to be selectively disengaged from the prosthesis, said attachment ring further comprising:

an inner ring member attached to the proximal ends of the strut members; and an outer ring member releasably attached to the inner ring member, a portion of said prosthesis being frictionally captured between the inner and outer ring members;

wherein the application of a force in a distal direction to the hub member subsequent to the detachment of the outer ring member from the inner ring member facilitates the distal movement of the inner ring member relative to the outer ring member thereby resulting in the separation of the inner and outer ring members from each other and the release of the portion of the prosthesis from therebetween.

32. The holding apparatus of claim 31, further comprising:

an elongate handle attachable to the hub member of the holding apparatus, and extendable in a distal direction therefrom.

33. The holding apparatus of claim 32 wherein said hub member has a female retention bore formed therein and wherein said elongate handle member has a distal male member formed thereon, the distal male member of said handle being engageable within the female retention bore of the hub member to effect attachment of said handle to said holding apparatus.

34. The holding apparatus of claim 31 wherein said inner and outer ring members are releasably attached to each other by at least one suture thread extending therebetween.

35. The holding apparatus of claim 34 wherein said inner and outer ring members each include at least one pair of suture passage apertures formed therein, the suture passage apertures of one pair being coaxially aligned with respective ones of the suture passage apertures of the other pair for permitting the suture thread to be extended between the inner and outer ring members.

36. The holding apparatus of claim 35 wherein said inner and outer ring members each include at least one enlarged attachment region formed thereon, each pair of the suture passage apertures being formed within a respective attachment region.

37. The holding apparatus of claim 36 wherein the attachment region formed on the inner ring member includes a cutting instrument receiving notch formed therein which is sized and configured to permit a cutting instrument to be inserted thereinto for purposes of cutting the suture thread.

38. The holding apparatus of claim 31 wherein:

said inner ring member defines a beveled outer surface portion; and said outer ring member defines a beveled inner surface portion having a configuration which is complementary to the outer surface portion of the inner ring member;

the portion of the prosthesis being frictionally captured between the outer and inner surface portions when the inner and outer ring members are releasably attached to each other.

39. The holding apparatus of claim 31 wherein said outer ring member includes at least one tab portion extending distally therefrom which is sized and configured to engage the inner ring member subsequent to the distal movement of the inner ring member relative to the outer ring member in an amount sufficient to release the portion of the prosthesis from therebetween.

40. The holding apparatus of claim 39 wherein:

said at least one strut member comprises three strut members spaced substantially equidistantly from one another.

41. The holding apparatus of claim 40 wherein said outer ring member includes three (3) pairs of tab portions extending distally therefrom, the tab portions of each pair being disposed on either side of a respective one of the strut members when the inner and outer ring members are attached to each other.

42. A heart valve prosthesis implantation system comprising the holding apparatus of claim 31, further in combination with a heart valve prosthesis disposed within the prosthesis retention space of said holding apparatus.

43. The system of claim 42 wherein said heart valve prosthesis is a stentless porcine bioprosthesis.

44. The system of claim 42 wherein said plurality of valving members disposed within the cylindrical prosthesis body comprise tricuspid valve leaflets.

45. The system of claim 44 wherein said heart valve prosthesis further comprises:

markers formed on said cylindrical prosthesis body, distal to said valve leaflets, to guide the optional cutting of the prosthesis body to remove a distal portion of the prosthesis body without injuring the valve leaflets.

46. A stentless aortic heart valve system incorporating the holding apparatus of claim 31, said system comprising:

a holding apparatus according to claim 31;

a stentless aortic bioprosthesis comprising a generally tubular prosthesis body having an inflow annulus at the proximal end thereof, an outflow annulus at the distal end thereof, a plurality of valving members disposed therewithin to hemodynamically valve blood passing through the tubular prosthesis body, and a mesh ring attached to the inflow annulus of the bioprosthesis;

said bioprosthesis being positioned within the prosthesis retention space of the holding apparatus, such that the mesh ring of the bioprosthesis protrudes beyond the proximal end of the holding apparatus.

47. The holding apparatus of claim 31 wherein the hub member positionable adjacent the distal end of the prosthesis body is configured so as not to block the entire outflow annulus of the bioprosthesis positioned within the holding apparatus, thereby allowing one to see the orientation of the valve leaflets by looking downwardly through the outflow annulus of the bioprosthesis.

48. The holding apparatus of claim 31 wherein said attachment ring is attached to the bioprosthesis in such a manner as to rigidly hold the bioprosthesis in a fully open configuration, thereby deterring the formation of plications in the bioprosthesis during the implantation procedure.

49. A method for implanting a prosthetic heart valve having a generally cylindrical prosthesis body, an inflow aperture formed at a proximal end of the generally cylindrical prosthesis body, an outflow aperture formed at the distal end of the prosthesis body, a plurality of valving members disposed within the prosthesis body, and a longitudinal axis projectable longitudinally through the prosthesis body, said method comprising the steps of:

a) providing a holding apparatus which comprises a rigid body having a distal end, a proximal end and a hollow heart valve prosthesis retention space defined therewithin, and an attachment ring disposed on the proximal end of the body for releasably connecting a heart valve prosthesis mounted within the prosthesis retention space to the holding apparatus.

b) positioning the heart valve prosthesis within the prosthesis retention space of the holding apparatus, said heart valve prosthesis having a distal end and a proximal end, an outflow annulus being formed at the proximal end thereof;

c) utilizing the attachment ring to temporarily connect at least the proximal end of the body to at least the proximal end of the prosthesis;

d) positioning the holding apparatus, with the heart valve prosthesis releasably mounted therewithin, a spaced distance away from an intended implantation site in the body of a patient with the proximal end of the prosthesis closest to the implantation site;

e) passing a plurality of suture threads through the intended implantation site in the body of the patient and through the inflow annulus of the heart valve prosthesis;

f) pushing the distal end of the body toward the implantation site, to advance the holding apparatus, with the heart valve prosthesis releasably mounted therein, over the previously placed suture threads, to a position where the inflow annulus of the heart valve prosthesis is in contact with the intended implantation site within the body of the patient;

g) causing the attachment ring to release the heart valve prosthesis from its connection with the holding apparatus; and h) extracting and removing the holding apparatus, leaving the heart valve prosthesis at the intended implantation site.

50. The method of claim 49 wherein said method further comprises:

i) tying and cutting the previously placed suture threads to secure the inflow annulus of the heart valve prosthesis to the intended implantation site of the patient.

51. The method of claim 50 wherein said method further comprises the step of:

suturing the outflow aperture at the distal end of the heart valve prosthesis to the body of the patient, at a location which is downstream of the site at which the inflow aperture of the prosthesis was sutured to the body of the patient.

52. The method of claim 51 wherein the bioprosthesis has right and left coronary openings formed therein at locations which correspond to the right and left coronary ostia of the patient, and wherein the method further comprises the step of:

j) suturing the coronary openings of the prosthesis to the aortic tissue of the patient such that the coronary openings of the prosthesis are in alignment with the patient's coronary ostia, thereby allowing a portion of the blood which passes out of the outflow annulus of the prosthesis to flow into the coronary arteries of the patient.

53. A holding apparatus for facilitating the surgical implantation of a heart valve prosthesis of the type having, i) a generally tubular prosthesis body having an inner surface, an outer surface, a proximal end, a distal end, an inflow annulus at the proximal end thereof, an outflow annulus at the distal end thereof, and ii) a plurality of valving members disposed within the prosthesis body to perform a hemodynamic valving function and a sewing ring attached to the inflow annulus to facilitate suturing of the inflow annulus to an endogenous opening, said holding apparatus comprising:

a) a hub member positionable adjacent the distal end of the prosthesis body b) a plurality of elongate strut members having proximal ends and distal ends which are attached to said distal hub member such that the strut members extend substantially downward therefrom so as to define a hollow prosthesis retention space inboard of said strut members and beneath said hub member;

c) at least one releasable attachment means for releasably holding the prosthesis within said prosthesis retention space such that the proximal inflow end of the prosthesis is connected to the strut members;

d) a plurality of first suture threads anchored to the proximal ends of the strut members of the holding apparatus, the first suture threads being passed through the inflow annulus at the proximal end of a heart valve prosthesis disposed within the hollow prosthesis retention space of the holding apparatus to connect the proximal ends of the strut members to the inflow annulus of the prosthesis; and, e) a plurality of second suture threads anchored to the distal hub member of the holding apparatus, the second suture threads being passed through the heart valve prosthesis at locations which are distal to the proximal end of the prosthesis to effect further connection of the prosthesis to the holding apparatus, wherein, a portion of each of said first and second suture threads being passed through and positioned in side-by-side juxtaposition at first locations on the holding apparatus which are sufficiently accessible during the implantation procedure to permit concurrently severing by a cutting instrument of said first and second suture threads at said first locations, thereby causing the prosthesis to be disconnected from the holding apparatus such that the holding apparatus may be subsequently extracted and removed, leaving the heart valve prosthesis in place.

54. The holding apparatus of claim 53 wherein a suture retainer is formed on each of said strut members, and wherein said first suture threads and said second suture threads are passed through said suture retainer in side-by-side juxtaposition, such that said first and second suture threads may be simultaneously cut by a single cutting action performed at the location of said suture retainer.

55. The holding apparatus of claim 54 wherein a cutting instrument receiving slot is formed in said holding apparatus, in the region of said suture retainer, to permit a cutting instrument to be inserted for the purpose of cutting said first and second suture threads at the location of said suture retainer.

56. A holding apparatus for facilitating the surgical implantation of a heart valve prosthesis of the type having, i) a generally tubular prosthesis body having an inner surface, an outer surface, a proximal end, a distal end, an inflow annulus at the proximal end thereof, an outflow annulus at the distal end thereof, and ii) a plurality of valving members disposed within the prosthesis body to perform a hemodynamic valving function and a sewing ring attached to the inflow annulus to facilitate suturing of the inflow annulus to an endogenous opening, said holding apparatus comprising:

a) a hub member positionable adjacent the distal end of the prosthesis body and configured so as not to block the entire outflow annulus of the bioprosthesis positioned within the holding apparatus, thereby allowing one to see the orientation of the valve leaflets by looking downwardly through the outflow annulus of the bioprosthesis;

b) a plurality of elongate strut members having proximal ends and distal ends which are attached to said distal hub member such that the strut members extend substantially downward therefrom so as to define a hollow prosthesis retention space inboard of said strut members and beneath said hub member; and c) at least one releasable attachment means for releasably holding the prosthesis within said prosthesis retention space such that the proximal inflow end of the prosthesis is connected to the strut members.

57. The holding apparatus of claim 56, further comprising:

an elongate handle attachable to the distal hub member of the holding apparatus, and extendible in a distal direction therefrom.

58. The holding apparatus of claim 57 wherein said distal hub member has a female retention bore formed therein and wherein said elongate handle member has a distal male member formed thereon, the distal male member of said handle being engageable within the female retention bore of the distal hub member to effect attachment of said handle to said holding apparatus.

59. The holding apparatus of claim 56 further comprising:

at least one releasable attachment member for temporarily connecting the inflow annulus at the proximal end of a heart valve prosthesis disposed within said hollow prosthesis retention space, to the proximal ends of the strut members;

said releasable attachment member being manually disconnectable from said prosthesis in a manner which releases the holding apparatus from said prosthesis.

60. The holding apparatus of claim 59 wherein:

said at least one releasable attachment member comprises a suture thread anchored to the holding apparatus and passable through a prosthesis which is disposed within the hollow prosthesis retention space, to releasably attach said prosthesis to said holding apparatus;

a portion of said suture thread being located upon the holding apparatus at a first location which is sufficiently accessible during the implantation procedure to permit cutting of said suture thread at said first location, thereby causing the prosthesis to be disconnected from the holding apparatus such that the holding apparatus may be subsequently extracted and removed, leaving the heart valve prosthesis in place.

61. The holding apparatus of claim 60 wherein said holding apparatus further comprises:

a cutting instrument retention notch formed in said holding apparatus at said first location;

said cutting instrument retention notch being sized to permit a cutting instrument to be inserted thereinto for the purpose of cutting of said suture thread at said first location.

62. The holding apparatus of claim 56 wherein:

said at least one strut member comprises three strut members spaced substantially equidistant from one another.

63. A heart valve prosthesis implantation system comprising the holding apparatus of claim 56, further in combination with a heart valve prosthesis disposed within the prosthesis retention space of said holding apparatus.

64. The system of claim 63 wherein said heart valve prosthesis is a stentless porcine bioprosthesis.

65. A stentless aortic heart valve system incorporating the holding apparatus of claim 56, said system comprising:

a holding apparatus according to claim 56;

a stentless aortic bioprosthesis comprising a generally tubular prosthesis body having an inflow annulus at the proximal end thereof, an outflow annulus at the distal end thereof, a plurality of valving members disposed therewithin to hemodynamically valve blood passing through the tubular prosthesis body, and a mesh ring attached to the inflow annulus of the bioprosthesis;

said bioprosthesis being positioned within the prosthesis retention space of the holding apparatus, such that the mesh ring of the bioprosthesis protrudes beyond the proximal end of the holding apparatus.

66. The stentless aortic bioprosthesis system of claim 65 wherein:

a proximal ring member is formed on the bottom ends of the elongate strut members of the holding apparatus, said proximal ring member having a plurality of suture passage apertures formed therein; and, at least one suture thread being passed in and out of the suture passage apertures formed in the proximal ring member of the holding apparatus and through the prosthesis body to effect releasable attachment of the proximal ring member of the holding apparatus to the prosthesis while the prosthesis is positioned within the retention space of the holding apparatus.

67. The stentless aortic bioprosthesis system of claim 66 wherein the proximal ring member of the holding apparatus is separable into a plurality of segments after it has been disconnected from the prosthesis.

68. A holding apparatus for facilitating the surgical implantation of a heart valve prosthesis of the type having, i) a generally tubular prosthesis body having an inner surface, an outer surface, a proximal end, a distal end, an inflow annulus at the proximal end thereof, an outflow annulus at the distal end thereof, and ii) a plurality of valving members disposed within the prosthesis body to perform a hemodynamic valving function and a sewing ring attached to the inflow annulus to facilitate suturing of the inflow annulus to an endogenous opening, said holding apparatus comprising:

a) a hub member positionable adjacent the distal end of the prosthesis body b) a plurality of elongate strut members having proximal ends and distal ends which are attached to said distal hub member such that the strut members extend substantially downward therefrom so as to define a hollow prosthesis retention space inboard of said strut members and beneath said hub member; and c) at least one releasable attachment means for releasably holding the prosthesis within said prosthesis retention space such that the proximal inflow end of the prosthesis is connected to the strut members, wherein, said plurality of elongate strut members and said releasable attachments are attached about the bioprosthesis in such a manner as to rigidly hold the bioprosthesis in a fully open configuration, thereby deterring the formation of plications in the bioprosthesis during the implantation procedure.

69. The holding apparatus of claim 68, further comprising:

an elongate handle attachable to the distal hub member of the holding apparatus, and extendible in a distal direction therefrom.

70. The holding apparatus of claim 69 wherein said distal hub member has a female retention bore formed therein and wherein said elongate handle member has a distal male member formed thereon, the distal male member of said handle being engageable within the female retention bore of the distal hub member to effect attachment of said handle to said holding apparatus.

71. The holding apparatus of claim 68 further comprising:

at least one releasable attachment member for temporarily connecting the inflow annulus at the proximal end of a heart valve prosthesis disposed within said hollow prosthesis retention space, to the proximal ends of the strut members;

said releasable attachment member being manually disconnectable from said prosthesis in a manner which releases the holding apparatus from said prosthesis.

72. The holding apparatus of claim 71 wherein:

said at least one releasable attachment member comprises a suture thread anchored to the holding apparatus and passable through a prosthesis which is disposed within the hollow prosthesis retention space, to releasably attach said prosthesis to said holding apparatus;

a portion of said suture thread being located upon the holding apparatus at a first location which is sufficiently accessible during the implantation procedure to permit cutting of said suture thread at said first location, thereby causing the prosthesis to be disconnected from the holding apparatus such that the holding apparatus may be subsequently extracted and removed, leaving the heart valve prosthesis in place.

73. The holding apparatus of claim 72 wherein said holding apparatus further comprises:

a cutting instrument retention notch formed in said holding apparatus at said first location;

said cutting instrument retention notch being sized to permit a cutting instrument to be inserted thereinto for the purpose of cutting of said suture thread at said first location.

74. The holding apparatus of claim 68 wherein:

said at least one strut member comprises three strut members spaced substantially equidistant from one another.

75. A heart valve prosthesis implantation system comprising the holding apparatus of claim 68, further in combination with a heart valve prosthesis disposed within the prosthesis retention space of said holding apparatus.

76. The system of claim 75 wherein said heart valve prosthesis is a stentless porcine bioprosthesis.

77. A stentless aortic heart valve system incorporating the holding apparatus of claim 68, said system comprising:

a holding apparatus according to claim 68;

a stentless aortic bioprosthesis comprising a generally tubular prosthesis body having an inflow annulus at the proximal end thereof, an outflow annulus at the distal end thereof, a plurality of valving members disposed therewithin to hemodynamically valve blood passing through the tubular prosthesis body, and a mesh ring attached to the inflow annulus of the bioprosthesis;

said bioprosthesis being positioned within the prosthesis retention space of the holding apparatus, such that the mesh ring of the bioprosthesis protrudes beyond the proximal end of the holding apparatus.

78. The stentless aortic bioprosthesis system of claim 77 wherein:

a proximal ring member is formed on the bottom ends of the elongate strut members of the holding apparatus, said proximal ring member having a plurality of suture passage apertures formed therein; and, at least one suture thread being passed in and out of the suture passage apertures formed in the proximal ring member of the holding apparatus and through the prosthesis body to effect releasable attachment of the proximal ring member of the holding apparatus to the prosthesis while the prosthesis is positioned within the retention space of the holding apparatus.

79. The stentless aortic bioprosthesis system of claim 78 wherein the proximal ring member of the holding apparatus is separable into a plurality of segments after it has been disconnected from the prosthesis.

80. A stentless aortic heart valve system incorporating a holding apparatus for facilitating the surgical implantation of a stentless heart valve prosthesis of the type having, i) a generally tubular prosthesis body having an inner surface, an outer surface, a proximal end, a distal end, an inflow annulus at the proximal end thereof, an outflow annulus at the distal end thereof, and ii) a plurality of valving members disposed within the prosthesis body to perform an hemodynamic valving function and a sewing ring attached to the inflow annulus to facilitate suturing of the inflow annulus to an endogenous opening, said system comprising:

a) a hub member positionable adjacent the distal end of the prosthesis body;

b) a plurality of elongate strut members having proximal ends and distal ends which are attached to said hub member such that the strut members extend substantially downward therefrom so as to define a hollow prosthesis retention space inboard of said strut members and beneath said hub member; and c) an attachment ring disposed on the proximal ends of the strut members for maintaining the prosthesis within said prosthesis retention space, the proximal inflow end of the prosthesis being releasably connected to the attachment ring to allow the holding apparatus to be selectively disengaged from the prosthesis, said stentless aortic bioprosthesis having a mesh ring attached to the inflow annulus of the bioprosthesis and being positioned within the prosthesis retention space of the holding apparatus, such that the mesh ring of the bioprosthesis protrudes beyond the proximal end of the holding apparatus.

81. A holding apparatus for facilitating the surgical implantation of a heart valve prosthesis of the type having, i) a generally tubular prosthesis body having an inner surface, an outer surface, a proximal end, a distal end, an inflow annulus at the proximal end thereof, an outflow annulus at the distal end thereof, and ii) a plurality of valving members disposed within the prosthesis body to perform an hemodynamic valving function and a sewing ring attached to the inflow annulus to facilitate suturing of the inflow annulus to an endogenous opening, said holding apparatus comprising:

a) a hub member positionable adjacent the distal end of the prosthesis body and configured so as not to block the entire outflow annulus of the bioprosthesis positioned within the holding apparatus, thereby allowing one to see the orientation of the valve leaflets by looking downwardly through the outflow annulus of the bioprosthesis;

b) a plurality of elongate strut members having proximal ends and distal ends which are attached to said hub member such that the strut members extend substantially downward therefrom so as to define a hollow prosthesis retention space inboard of said strut members and beneath said hub member; and c) an attachment ring disposed on the proximal ends of the strut members for maintaining the prosthesis within said prosthesis retention space, the proximal inflow end of the prosthesis being releasably connected to the attachment ring to allow the holding apparatus to be selectively disengaged from the prosthesis.

82. A holding apparatus for facilitating the surgical implantation of a heart valve prosthesis of the type having, i) a generally tubular prosthesis body having an inner surface, an outer surface, a proximal end, a distal end, an inflow annulus at the proximal end thereof, an outflow annulus at the distal end thereof, and ii) a plurality of valving members disposed within the prosthesis body to perform an hemodynamic valving function and a sewing ring attached to the inflow annulus to facilitate suturing of the inflow annulus to an endogenous opening, said holding apparatus comprising:

a) a hub member positionable adjacent the distal end of the prosthesis body;

b) a plurality of elongate strut members having proximal ends and distal ends which are attached to said hub member such that the strut members extend substantially downward therefrom so as to define a hollow prosthesis retention space inboard of said strut members and beneath said hub member; and c) an attachment ring disposed on the proximal ends of the strut members for maintaining the prosthesis within said prosthesis retention space, the proximal inflow end of the prosthesis being releasably connected to the attachment ring to allow the holding apparatus to be selectively disengaged from the prosthesis, wherein, said attachment ring is attached to the bioprosthesis in such a manner as to rigidly hold the bioprosthesis in a fully open configuration, thereby deterring the formation of plications in the bioprosthesis during the implantation procedure.

* * * * *